US011363992B2

(12) United States Patent
Alphonse et al.

(10) Patent No.: US 11,363,992 B2
(45) Date of Patent: Jun. 21, 2022

(54) WEARABLE DEVICE UTILIZING FLEXIBLE ELECTRONICS

(71) Applicant: Advancing Technologies, LLC, Ocoee, FL (US)

(72) Inventors: Ricky Alphonse, Ocoee, FL (US); Kelsey Melrose, Lexington, KY (US); Catherine Chou, Vancouver (CA); Noah Schimmel, Woodstock, GA (US); Ramamurthy Siripuram, Wilton, CT (US); Anthony Tran, Cumming, GA (US); Britny Farahdel, Duluth, GA (US); Dalton Smith, Tallapoosa, GA (US); Danice Wang, Cumming, GA (US); Kunal Mehan, Atlanta, GA (US); Theodore Virtue, Farmingdale, NJ (US)

(73) Assignee: ADVANCING TECHNOLOGIES, LLC, Ocoee, FL (US)

( * ) Notice: Subject to any disclaimer, the term of this patent is extended or adjusted under 35 U.S.C. 154(b) by 289 days.

(21) Appl. No.: 16/209,906

(22) Filed: Dec. 4, 2018

(65) Prior Publication Data
US 2019/0183430 A1 Jun. 20, 2019

Related U.S. Application Data

(60) Provisional application No. 62/594,498, filed on Dec. 4, 2017.

(51) Int. Cl.
A61B 5/0205 (2006.01)
A61B 5/00 (2006.01)
(Continued)

(52) U.S. Cl.
CPC .......... A61B 5/7275 (2013.01); A61B 5/0002 (2013.01); A61B 5/0205 (2013.01);
(Continued)

(58) Field of Classification Search
None
See application file for complete search history.

(56) References Cited

U.S. PATENT DOCUMENTS 5,906,638 A * 5/1999 Shimoda .................. A61N 1/10 607/1
2014/0275812 A1 * 9/2014 Stivoric .................... A61B 5/01 600/300

(Continued)

Primary Examiner — Ankit D Tejani
(74) Attorney, Agent, or Firm — Mammen ("Roy") P. Zachariah, Jr.; Greenberg Traurig LLP

(57) ABSTRACT

A wearable device utilizing flexible electronics is disclosed. The wearable device may comprise a flexible matrix material and may include sensors for measuring biometric measurements of an individual, an accelerometer for measuring an acceleration of a body part to which the wearable device is attached, a wireless transmitter, a flexible power source, and a microcontroller. During an activity, the microcontroller may receive signals from the sensors including the biometric measurements, and signals from the accelerometer including acceleration and force measurements associated with the individual. The microcontroller may convert the signals into digital signals and transmit the signals to a computing device for analysis. The computing device may analyze the digital signals to determine a performance metric for the individual. The performance metric may be compared to baseline data for the individual to determine a fatigue level, injury risk, or an adjustment to be made by the individual during the activity.

11 Claims, 17 Drawing Sheets

(51) Int. Cl.
*A61B 5/145* (2006.01)
*A61B 5/11* (2006.01)
*A61B 5/22* (2006.01)
*A61B 5/024* (2006.01)

(52) U.S. Cl.
CPC ........ *A61B 5/02438* (2013.01); *A61B 5/1118* (2013.01); *A61B 5/14514* (2013.01); *A61B 5/14542* (2013.01); *A61B 5/22* (2013.01); *A61B 5/4875* (2013.01); *A61B 5/6802* (2013.01); *A61B 5/7235* (2013.01); *A61B 5/7278* (2013.01); *A61B 5/742* (2013.01); *A61B 5/746* (2013.01); *A61B 5/024* (2013.01); A61B 5/02405 (2013.01); A61B 5/6833 (2013.01); A61B 2560/0214 (2013.01); A61B 2562/0219 (2013.01); A61B 2562/164 (2013.01)

(56) References Cited

U.S. PATENT DOCUMENTS

| | | | | |
|---|---|---|---|---|
| 2015/0065841 | A1* | 3/2015 | Lee | A61B 5/0245 |
| | | | | 600/388 |
| 2016/0226542 | A1* | 8/2016 | Tran | A61B 5/02438 |
| 2017/0319133 | A1* | 11/2017 | Coza | G16H 40/67 |
| 2019/0077007 | A1* | 3/2019 | Mallinson | A61B 5/1118 |

* cited by examiner

WEARABLE DEVICE UTILIZING FLEXIBLE ELECTRONICS

CROSS REFERENCE TO RELATED APPLICATIONS

The present application claims priority to and the benefit of U.S. Provisional Patent Application No. 62/594,498, filed Dec. 4, 2017, the entirety of which is hereby incorporated by reference.

FIELD OF THE INVENTION

The present application relates to wearable device technologies, flexible device technologies, performance analysis technologies, data aggregation, manipulation, and analysis technologies, and computing technologies, and more particularly, to a wearable device utilizing flexible electronics.

BACKGROUND

In today's technologically-driven society, various systems and methods exist for tracking and monitoring an individual's health while performing an activity. For example, users utilize smart watches and other activity trackers that measure the number of steps walked, a user's heart rate, a number of steps climbed, along with other metrics. While such devices may be suitable for tracking activity metrics for casual users, such devices are not suitable for all types of activities or professional sports. In particular, there is currently a problem in professional sports where athletes, teams, trainers and doctors desire to gather data on users, however, the form factor of current tracking devices remains an obstacle. Existing athletic wearable devices typically utilize a wrist band based form factor and, unfortunately, due to safety reasons, these devices are deemed illegal to use in competition by either leagues, commissions, or other regulatory bodies. Even if these devices are legal, their rigid form factor leaves room for damage to the device itself, the user, or even their competitors. Many existing wearable devices only perform a few tasks, and, as a result, users need to wear a combination of multiple devices having different capabilities to achieve their overall goals. Additionally, athletes in many sports do not have the ability to gauge performance, monitor workload or access health and injury risks. Trainers rely simply on gauging athletic performance based on the naked eye with no quantified data to rely on. The same may be said for strength and conditioning coaches, and even nutritionists.

In most sporting genres, users wear articles of clothing and various forms of gear. As technology has evolved, various forms of sports have attempted to take advantage of technological advancements to improve their leagues, improve athlete safety, and find new ways to engage fans. Companies began using articles of clothing such as shirts and shorts as a place to embed circuitry that contained sensors to measure athletic and biometric performance. In football, for example, RFID chips are embedded in a user's shoulder pads to monitor a football player's on-field speed and to track their on-field location. Unfortunately, in the world of combat sports, such as boxing, Muay Thai, karate, kickboxing, wrestling, and MMA, the only articles of clothing worn by male competitors are socks, shoes and shorts. Female competitors also wear tops in addition to shorts, shoes and socks, however, placing circuitry in a sports bra leaves it prone to being broken due to punches or kicks potentially impacting the sensors and the device's components. As a result, trainers and others are often relegated to visually assessing a user's performance during an activity by using only their eyes. Nevertheless, even if such users utilize existing wearable devices, such existing wearable device do not address athlete safety or the ability to track their health effectively. Additionally, existing wearable devices fail to assess injury risk or fatigue levels. The form factors of existing wearable devices do not permit multifaceted usage, and, from a user standpoint, these form factors represent materials that are foreign to the materials that combat athletes use on a daily basis. As a result, this makes user adoption a more difficult task. For example, during a normal training session, a boxer may wear different sized gloves for different activities. Each time gloves are changed the devices that are currently available also need to be readjusted for the next activity. If the boxer then engages in strength and conditioning training, they would then need to remove the devices they are wearing and place another device, such as a heart rate band on their body. Given that current devices are not multi-faceted, a user can be placed in a precarious situation when sparring or during an actual match because current devices do not provide real-time biometric readings. Furthermore, all combat sports other than boxing require participants to not only utilize punches but also to utilize kicks, and, in some cases, elbows and knees. Existing wearable devices do not give athletes the ability to access data on kicks, knees, elbows, and/or other body parts due to their form factors. As a result, a user may lack the data necessary to fully prepare for an opponent.

Even though various systems and methods exist for monitoring a user's performance during an activity, such systems and methods are often difficult for users to utilize and do not provide enough relevant information relating to the user's performance. Additionally, current technologies and processes are often error-prone, provide a lot of irrelevant information, require the accessing of data scattered across multiple and disparate devices, and may be difficult to implement. Moreover, currently existing technologies have not provided optimal ways of tracking a user's performance, injury risk, or improvements. As a result, current technologies and processes may be modified and improved so as to provide enhanced functionality and features for users and systems to monitor a user's performance in an expeditious and effective manner. Such enhancements and improvements may provide for improved performance over time, improved user satisfaction, increased efficiencies, increased access to meaningful data, substantially-improved decision-making abilities for trainers and users, and increased ease-of-use for users.

SUMMARY

Flexible wearable devices and systems and methods for utilizing the flexible wearable devices for monitoring and tracking a user's performance are disclosed. The flexible wearable device includes flexible componentry, which facilitates effective tracking of user biometrics and acceleration data to effectively monitor a user's performance during an activity. The flexible wearable devices provide the ability to not only gather feedback on technique and performance, but the flexible wearable devices also provide a form factor that allows for the gathering of additional data such as, but not limited to, fatigue levels and other biometric readings. This is accomplished by placing the device in a form factor that mimics materials that combat athletes use on a daily basis, such as tape. Using nanotechnology to shrink the devices footprint, additional sensors are incorporated into the wearable devices to gather additional readings, thus allowing a multi-faceted device that also allows users to customize their experience.

Additionally, the flexible wearable devices allow for seamless transitions between the various forms of training a combat athlete may engage in. The flexible wearable devices have a small footprint and form factor that allow a user to perform all activities while never having to worry about removing the device. Users of the flexible wearable devices are also given the comfort of not having to use other equipment to measure the other aspects of their training, such as having to also use a heart rate band during strength and conditioning training. Being multi-faceted means users are able to use these flexible wearable devices and have their safety monitored when they participate in an activity to avoid unfortunate situations, such as having their heart fail during a match. Furthermore, the flexible wearable devices allow a user to not only measure what their arms do but also their other body parts, such as, but not limited to, their legs, head, thighs, calves, feet, other various muscle groups and other body parts. As a result, the flexible wearable device's form factor allows the measurement of not only punches, but also kicks and/or any other movements. As a result, users can have a fully quantified training experience where they are measuring every aspect of their training.

The flexible wearable devices and the accompanying systems disclosed herein serve as a platform to measure athletic performance, reduce the risk of injury, and ensure safety. The platform consists of wearable devices that connect to a mobile device application, computer, tablet, smart glasses, augmented reality devices, virtual reality devices (e.g. headsets), and/or smart watches via a short-range wireless protocol, such as Bluetooth™, and/or via RFID technologies and/or other similar technologies. The devices' form factor, adhesive nature and onboard sensors allows them to be used in any sport as the accompanying software application (e.g mobile application) would simply need sport-specific software changes. The devices and accompanying software functionality of the systems may be utilized by combat sport athletes, their trainers, and nutritionists. For combat athletes, the devices may allow for them to customize their experience by placing the wearable devices on the area of their body where they want to gather feedback. A kick boxer, for example, would be able to place the device on the back of their heel and gather feedback on the speed of their kicks as well as the force associated with their kicks. The same goes for their punches when the device is placed on their wrist. Placing the device on the user's skin, due to its form factor, which is flexible and adhesive, allows for biometric readings. As a result, for the best heart rate readings, the kickboxer may place the adhesive patches on the areas deemed to get the strongest readings, such as on the underside of the wrist. The kickboxer may also be able to gather data, such as, but not limited to, oxygen and hydration levels. Therefore, as this device is placed under the wrist, he or she will be able to throw punches and gather feedback on the force, speed, what type of punch was thrown, what landed/missed and technique, along with how their body is reacting biometrically to the movements. The scenario above works the same for kicks, elbows, knees, and/or other movements as well. Notably, while the kickboxer is engaging in training, a proprietary algorithm may be executed that takes into account his or her performance and biometrics and compares them to baseline data to derive a fatigue metric. The fatigue metric can be accessed by trainers, nutritionists, and team doctors to prevent injuries and/or bodily harm. Additionally, a team doctor can review the data and/or the users can bring their biometric data to their primary care physicians and/or specialist, or have their biometric data automatically uploaded to their patient portal or medical records. A user's nutritionist can upload their meal plan, supplements, and liquid consumption to the platform/application and have their diet tie into their performance and biometric data to see their diet and regimen's affect in training and on their weight cut. This all allows the nutritionist to adjust the athlete's diet and supplementation accordingly.

The platform is significant due to the fact that it utilizes a first of its kind wearable device using flexible electronics for combat sports that also has the ability to work with any other type of sport in the future with simple software adjustments. The flexible wearable device and accompanying system takes into account each aspect of a user's training and serves as a platform for all of their uses. Trainers can gather performance data and come up with game plans. Nutritionists can log into the platform to enter diet plans and use the performance and biometric data to access what changes need to be made. Strength and conditioning coaches can also access all of the various data, such as the performance and biometric data to access weak points that need to be fine-tuned. Doctors can utilize the biometric data to ensure users are healthy and reduce potential injuries so a user's personal doctor can be sent reports or alerts, while not even having to visit the user in the gym. Notably, athletes that are participating in combat sports are at risk of many grave dangers due to the various aspects of the sport. The flexible wearable devices disclosed herein take into account the issues that plague combat athletes, such as the routine of dehydrating themselves to make weight, and monitoring their heart and oxygen levels. Currently, in combat sports, there are no real-time biometric devices being used during events or even during actual combat due to the current build and form factor of existing wearables. The flexible wearable device and system helps the user and every member of their camp not only visualize their performance, but also manage their safety by helping them visualize how they are performing biometrically. The device not only has a first of its kind form factor that feels natural, it also provides first of its kind data—the type of data to potentially save lives.

By utilizing proprietary algorithms, artificial intelligence, and information obtained from the wearable devices, a profile of a fighter's attributes is created. Having a broad database will allow a fighter and his or her team to search for a sparring partner that best fits what they are looking for in someone who mimics their upcoming opponent. On the other hand, up and coming fighters or those looking to make money can log into the database of the system to find fighters that are looking for sparring partners. The database may include a way to handle financial payments from a fighter to their sparring partner, coaches or experts that come out to assist them with a training camp. The database can also be a way for up and coming fighters to make their talents known to different fight organizations or promoters and vice-versa the promoter who is scouting for new talent can look through the database and see an athlete with a unique set of skills and recruit them. Notably, this can also be accomplished using proprietary software of the system that creates a profile for each athlete and their attributes and ranks them by weight class or by any other desired parameter. Anyone scouting for new talent can find the top ranked men and women based on their overall profile or they can search by categories such as hardest puncher, fastest puncher, best stamina or hardest working, sparring data, reach, height, age etc. At the same time a fighter or athlete's manager can search through the same profiles or have access to their client's profiles and utilize the data to look for deals and negotiate deals with promoters and organizations, while also utilizing the athlete's data and abilities for marketing opportunities.

To that end, in one embodiment according to the present disclosure, a flexible wearable device is disclosed. The flexible wearable device may include a wireless transmitter, a sensor configured to measure a heart rate of an individual wearing the wearable device, an accelerometer configured to measure an acceleration of a body part of the individual to which the wearable device is attached, a flexible power source for providing power to the wearable device, and a microcontroller including a memory that stores instructions and a processor that executes the instructions to perform operations. The operations may include receiving, from the sensor, a first signal including the heart rate measured by the sensor while the individual is participating in an activity; receiving, from the accelerometer, a second signal including acceleration data corresponding to the acceleration of the body part of the individual while the individual is participating in the activity; converting the first and second signals into first and second digital signals respectively; processing the first and second digital signals; and transmitting, by utilizing the wireless transmitter, the first and second digital signals to a computing device for analysis, wherein the analysis of the computing device indicates a performance metric of the individual while participating in the activity. The flexible wearable device may also include a flexible ribbon, wherein the wireless transmitter, the sensor, the accelerometer, the flexible power source, and the microcontroller are mounted onto the flexible ribbon. Moreover, the flexible wearable device may include a flexible patch matrix material, wherein the flexible ribbon, the wireless transmitter, the sensor, the accelerometer, the flexible power source, and the microcontroller may be housed within the flexible patch matrix material, which may serve as a covering.

In another embodiment, a system for utilizing a flexible wearable device for monitoring performance of an individual is provided. The system may include a memory that stores instructions and a processor that executes the instructions to perform operations conducted by the system. The system may perform an operation that includes receiving, from a flexible wearable device worn by an individual while participating in an activity, a first digital signal from a microcontroller of the flexible wearable device that includes a heart rate measured by a sensor of the flexible wearable device. The system may proceed to perform an operation that includes receiving, from the flexible wearable device, a second digital signal from the microcontroller that includes acceleration data corresponding to an acceleration of a body part of the individual while the individual participates in the activity. The system may analyze the first and second digital signals and determine a performance metric of the individual based on analyzing the first and second digital signals. The system may proceed to perform an operation that includes comparing the performance metric to baseline data for the individual to determine a fatigue level for the individual. Based on the fatigue level, the system may perform an operation that includes generating an alert.

In another embodiment, a method for utilizing a flexible wearable device for monitoring performance and/or health conditions is disclosed. The method may include utilizing a memory that stores instructions, and a processor that executes the instructions to perform the various functions of the method. In particular, the method may include receiving, from a flexible wearable device worn by an individual while participating in an activity, a first digital signal from a microcontroller of the flexible wearable device that includes a heart rate measured by a sensor of the flexible wearable device. The method may also include receiving, from the flexible wearable device, a second digital signal from the microcontroller that includes acceleration data corresponding to an acceleration of a body part of the individual while the individual participates in the activity. The method may include analyzing the first and second digital signals and determining a performance metric of the individual based on analyzing the first and second digital signals. The method may further include comparing the performance metric to baseline data for the individual to determine a fatigue level for the individual. Based on the fatigue level, the method may include generating an alert.

According to yet another embodiment, another flexible wearable device is provided. The flexible wearable devices may include a wireless transmitter, a sensor configured to measure a heart rate of an individual wearing the wearable device, an accelerometer configured to measure an acceleration of a body part of the individual to which the wearable device is attached, a flexible power source for providing power to the wearable device, and a microcontroller including a memory that stores instructions and a processor that executes the instructions to perform operations of the wearable device. The operations may include receiving, from the sensor, a first signal including the heart rate measured by the sensor while the individual is participating in an activity; receiving, from the accelerometer, a second signal including acceleration data corresponding to the acceleration of the body part of the individual while the individual is participating in the activity; converting the first and second signals into first and second digital signals respectively; processing the first and second digital signals; and transmitting, by utilizing the wireless transmitter, the first and second digital signals to a computing device for analysis. The analysis performed by the computing device may indicate a performance metric of the individual while participating in the activity. The wearable device may further include a housing tray, wherein the wireless transmitter, the sensor, the accelerometer, the flexible power source, and the microcontroller are included within the housing tray. Moreover, the wearable device may include a flexible patch matrix material. The housing tray, the wireless transmitter, the sensor, the accelerometer, the flexible power source, and the microcontroller may be housed within the flexible patch matrix material.

These and other features of the systems and methods for utilizing flexible wearable devices for monitoring performance of users are described in the following detailed description, drawings, and appended claims.

DETAILED DESCRIPTION OF THE INVENTION

Figure 1:
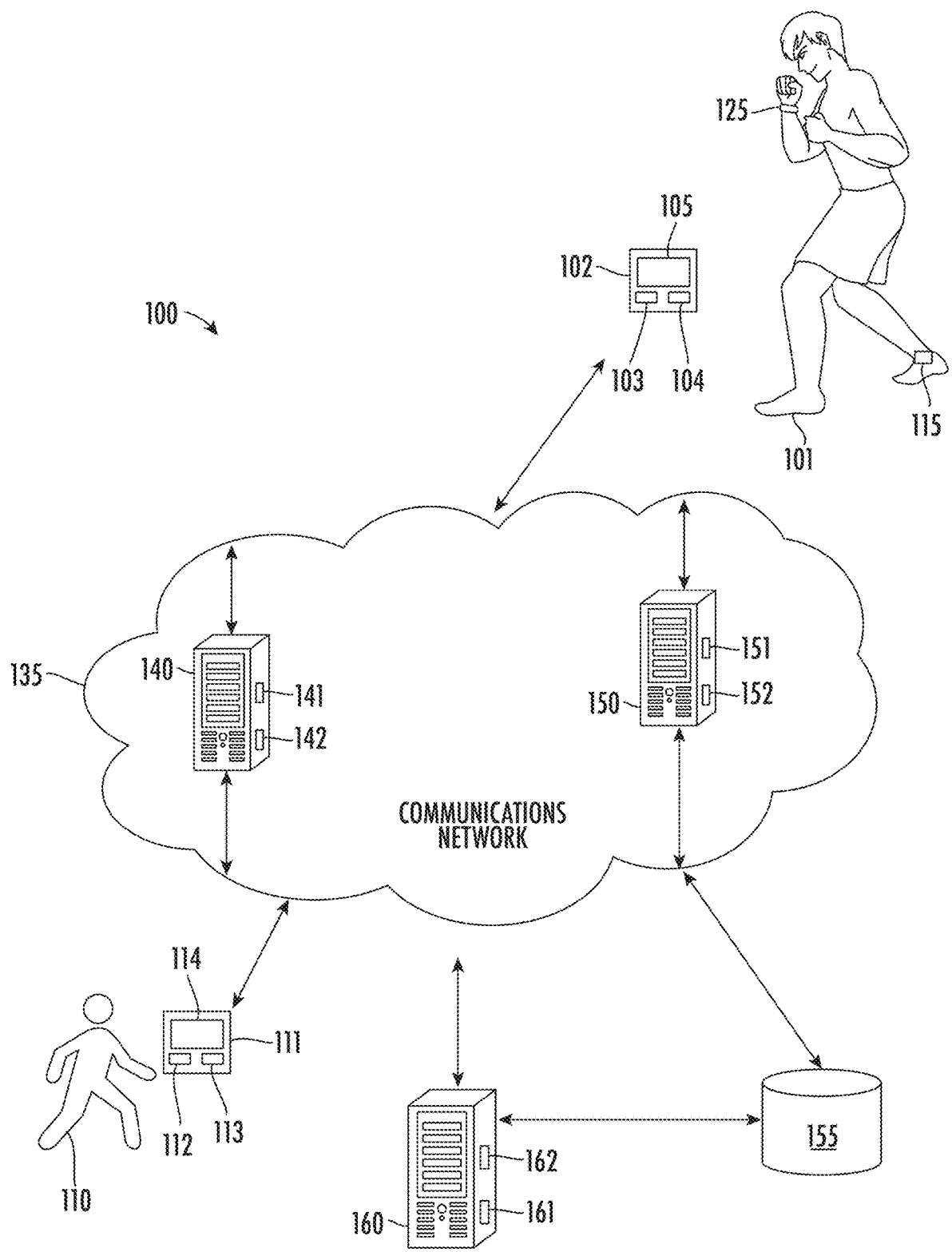
FIG. 1 is a schematic diagram of a system utilizing flexible wearable devices for monitoring performance of users according to an embodiment of the present disclosure.
Figure 2:
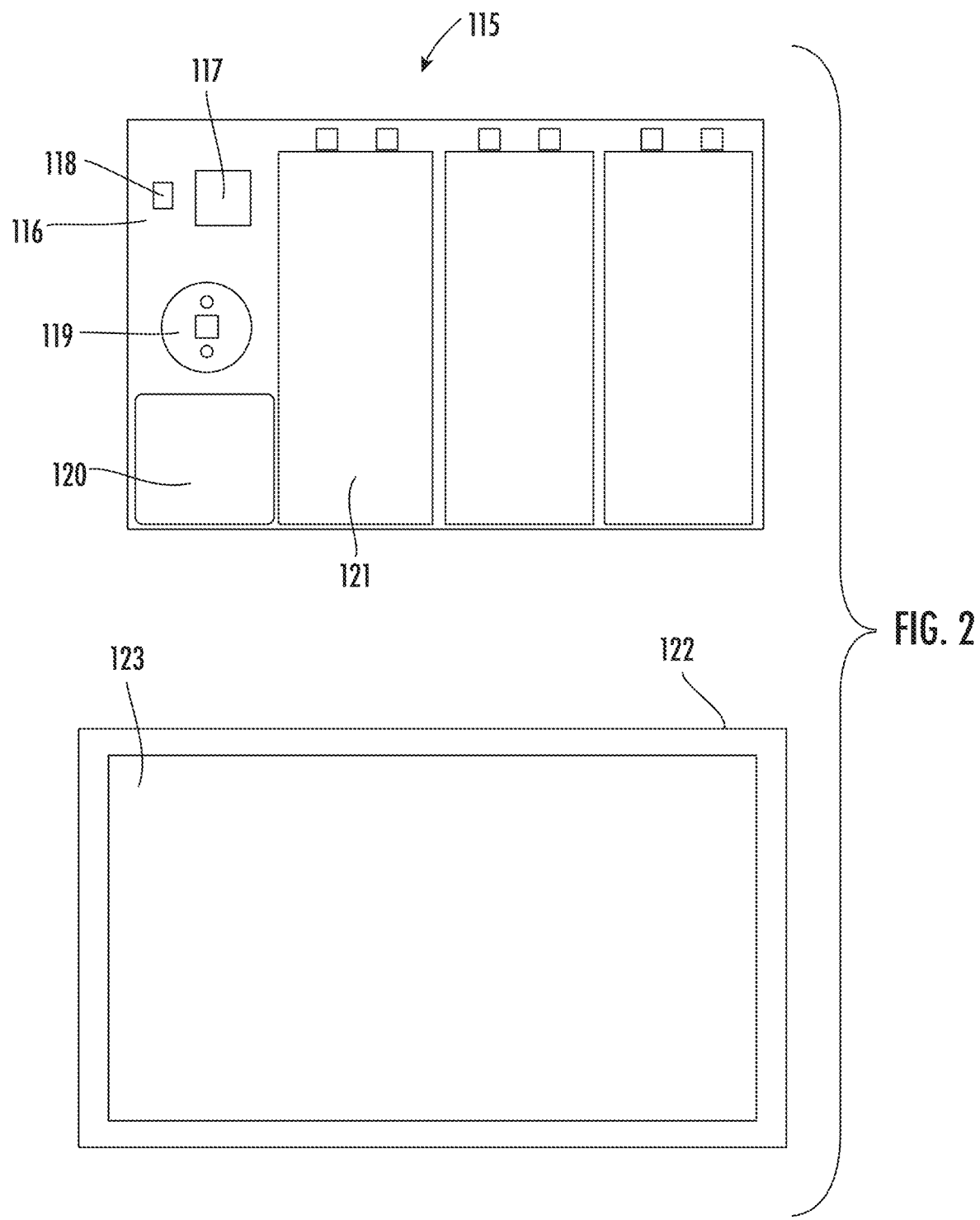
FIG. 2 is a schematic diagram illustrating a top view of various features and components of a flexible wearable device for use in the system of FIG. 1.
Figure 3:
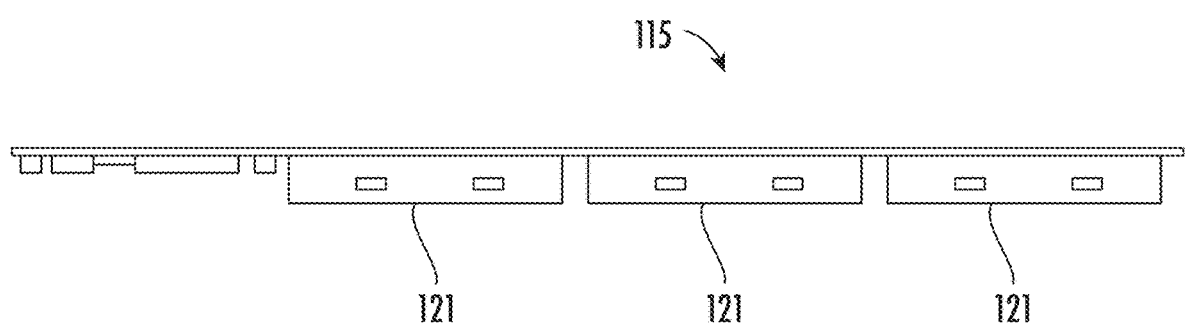
FIG. 3 is a schematic diagram illustrating a side view of various features and components of the flexible wearable device of FIG. 2.
Figure 4:
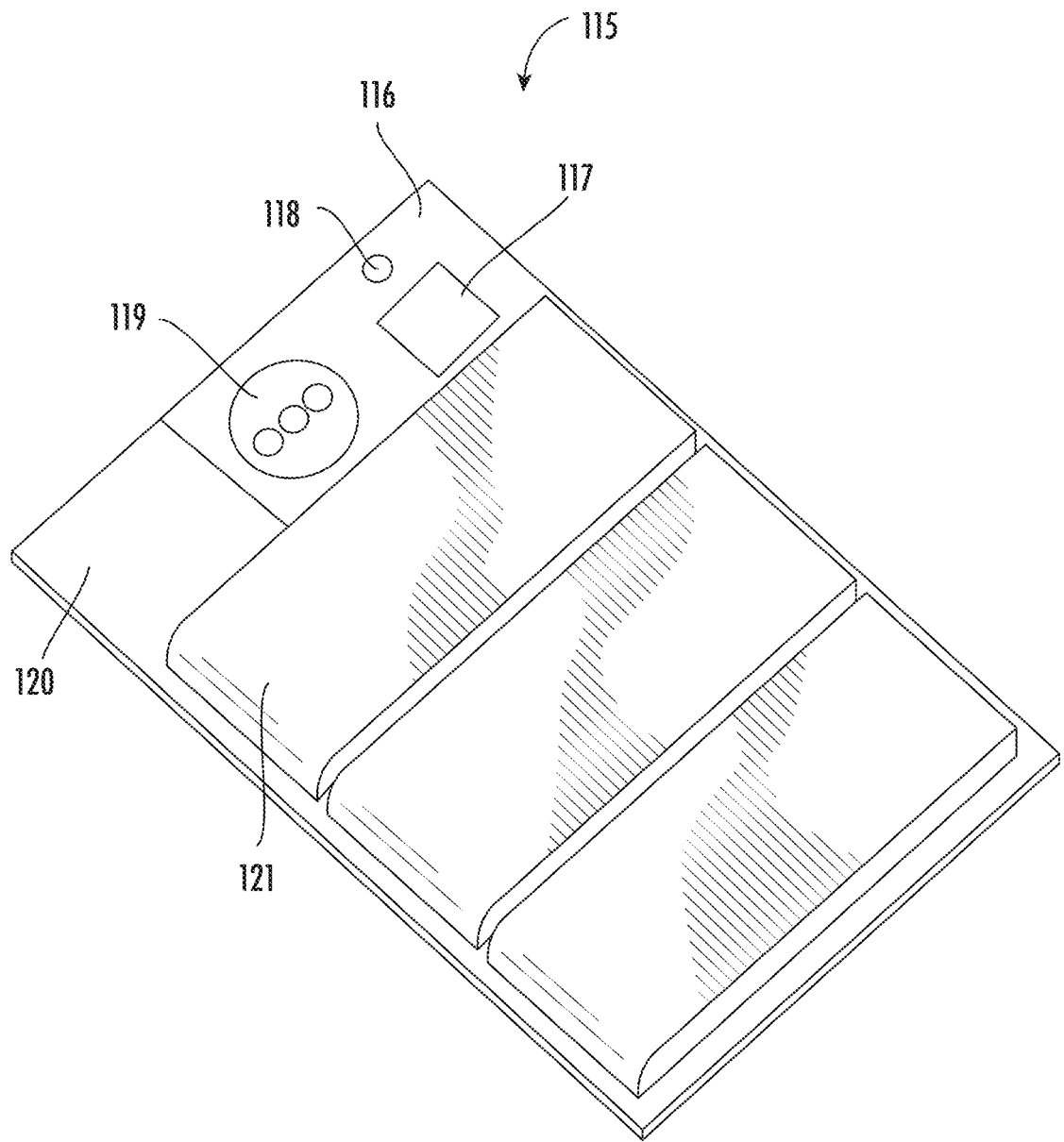
FIG. 4 is a schematic diagram illustrating an angled view of various features and components of the flexible wearable device of FIG. 2.
Figure 5:
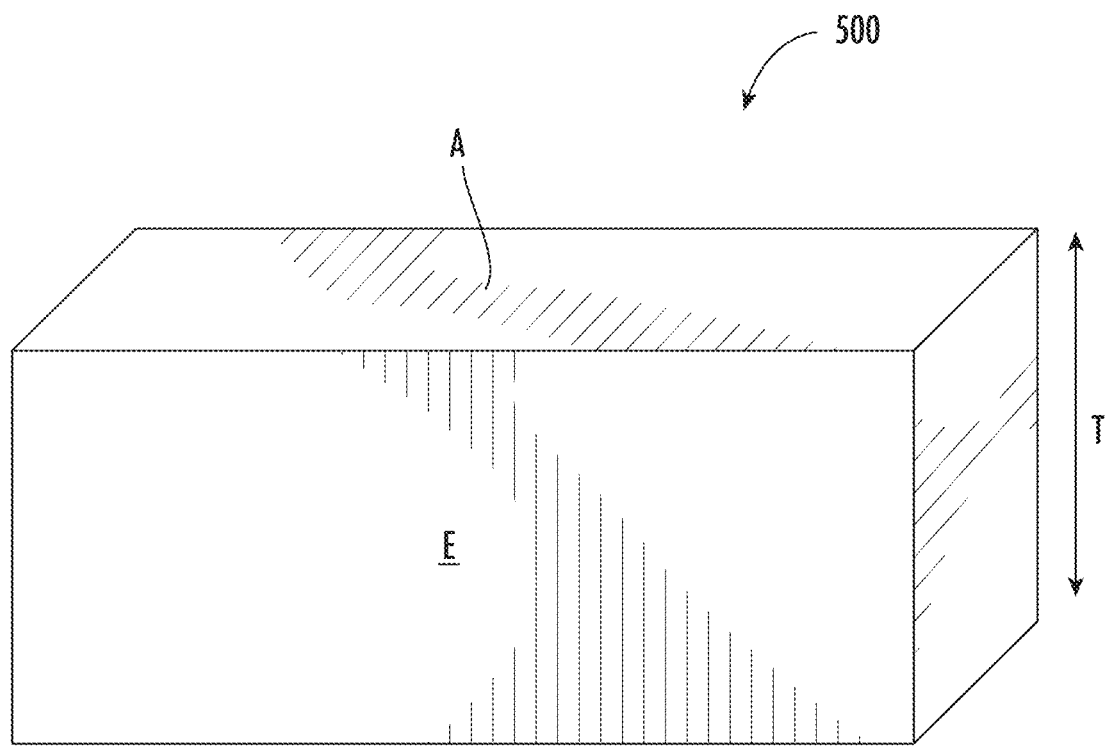
FIG. 5 is a schematic diagram illustrating reference dimensions utilized in a stress/strain analysis for a flexible wearable device for use with the system of FIG. 1.
Figure 6:
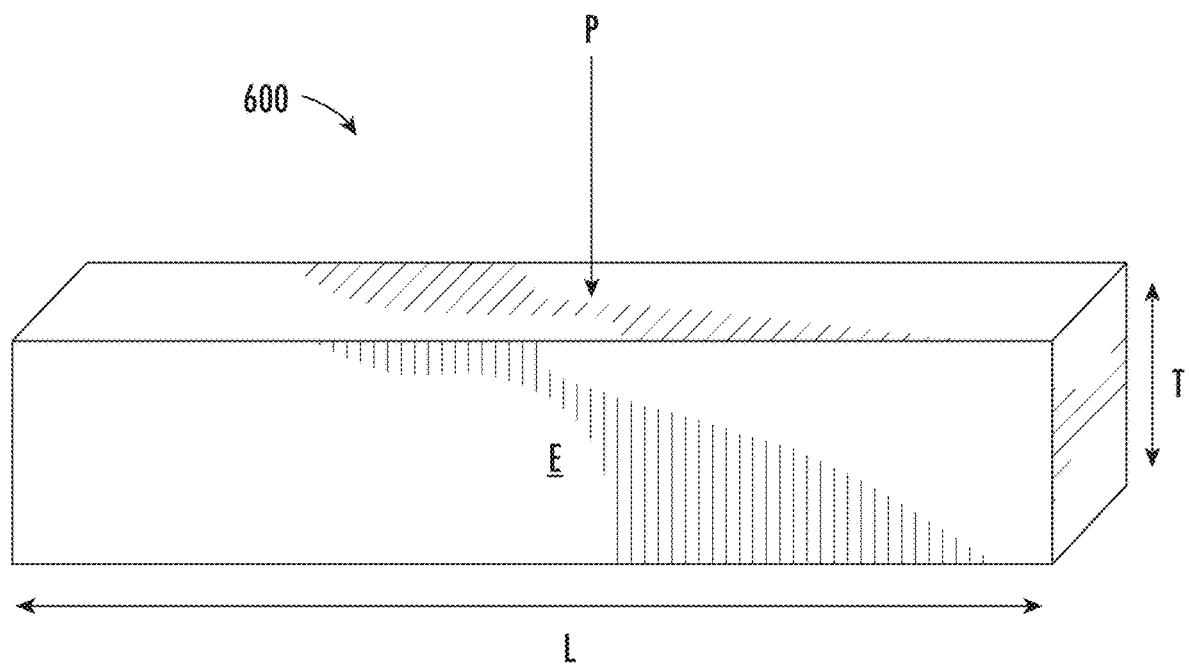
FIG. 6 is a schematic diagram illustrating reference dimensions utilized in a deflection analysis for a flexible wearable device for use with the system of FIG. 1.
Figure 7:
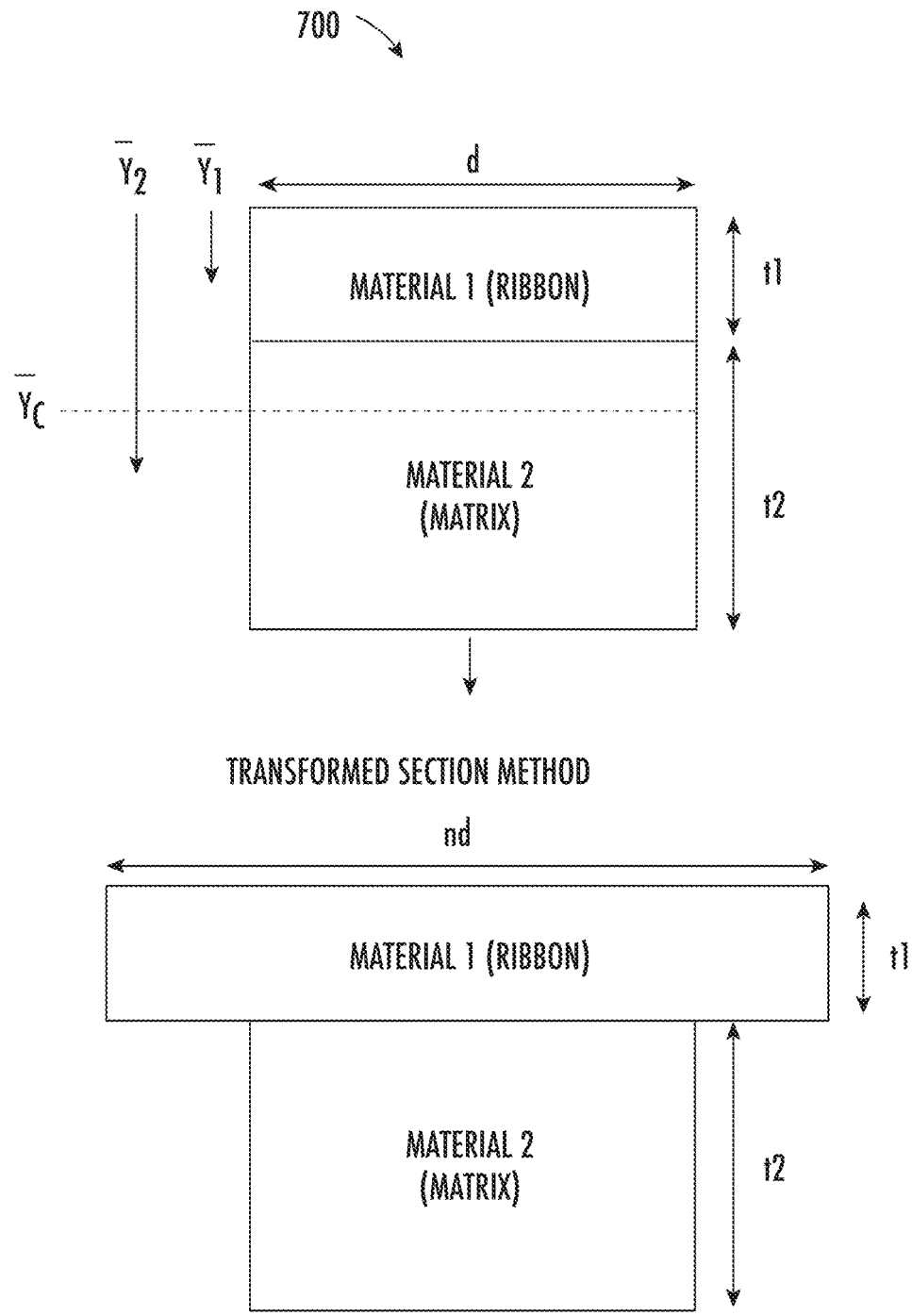
FIG. 7 is a schematic diagram illustrating transformed section method utilized for a stress analysis for a flexible wearable device for use with the system of FIG. 1.

Flexible wearable devices 115, 125, and a system 100 and methods for utilizing the flexible wearable devices 115, 125 to monitor performance are disclosed. In particular, flexible wearable devices 115, 125 may be placed on a user's skin, much like a bandage, kinesiology tape, a temporary tattoo or wearable tattoo, a sticker, or a nicotine patch that is not overly intrusive. Use of the flexible wearable devices 115, 125 also gives the user the ability to customize their experience, while utilizing the flexible wearable devices' 115, 125 adhesive nature to place it wherever they want to garner data feedback. For example, the flexible wearable devices 115, 125 may even be placed around a user's skull so as to obtain data on the rotational forces being issued to them during training or fights all while being able to build databases, study the impact of rotational forces and provide potential concussion awareness. In certain embodiments, the wearable devices 115, 125 can be placed behind the ear and in some embodiments may incorporate an EEG system to monitor brain activity. The flexible wearable devices 115, 125, along with their communication capabilities (e.g. Bluetooth, etc.) and the software functionality provided by the system 100, provide the ability to track the movements, performance, and biometrics of all users training in a gym at a particular time. All data can be accessed in real-time and the system 100 may generate troubling biometric warnings alerting those who need to be alerted if a risk of injury or fatigue is possible. The system 100 may also store data for historical viewing.

The sensors of the flexible wearable devices 115, 125 coupled with proprietary artificial intelligence algorithms determine fatigue metrics based on combining each individual's heart rate, oxygen level, hydration and performance metrics, such as, but not limited to, technique, punch/kick force and punch/kick speed. As training evolves and the body adapts, so too do the algorithms, such as via machine learning conducted in the system 100. The system 100 may include a full database of all kinds of body part movements. For example, the database 155 may include all left and right hand punches, which may include jabs, cross punches, hook punches, uppercuts, and other punches. Additionally, the database 155 may include all types of kicks and/or other body movements. The wearable device's 115, 125 sensors and artificial intelligence algorithms are accompanied by a constantly evolving database of fighting styles/moves, and the system 100 recognizes all of the various forms of movements, such as kicks. The sensors, devices, and/or the software functionality (e.g. software application) of the system 100 may recognize a user's stance and automatically recognizes what martial art is being utilized and all of the various forms of martial arts movements being made all of which are important for the various martial arts schools. The artificial intelligence algorithms and the system 100 may recognize when a new type of kick (or other movement) is performed, and may add that kick into the database 155. The new kick may be recognized with technique feedback when others attempt to perform the same move.

The wearable device's 115, 125 sensors, the algorithms, and the system 100 are utilized to build profiles so that when a user is in need of a sparring partner with a specific set of skills to either test them in areas or mimic an opponent, having steadily evolving data will produce the right individual to enter a camp to work with a particular user. As a result, the system 100 may establish a network that utilizes each user's evolving attributes recorded by the devices sensors and stored on the system's 100 database 155. For example, if a fighter whose main discipline is karate is in a training camp for an upcoming bout and is going to face a fighter whose specialty is Muy Thai and that opponent has certain dimensions and characteristics, using the system 100, an individual with all of those attributes may be recognized and located by using the system's 100 proprietary algorithms and the database 155 of fighters who have used the wearable devices and/or software applications of the system 100, at that point it will be easy for the karate fighters camp to reach out to that Muy Thai specialist for their service as a sparring partner to mimic the upcoming opponent. Using the same scenario as before, if a Muay Thai specialist and a karate expert trained together they would be able to see how they did against one another, while also receiving the feedback on how their opponent did against them, information indicating punches and kicks that landed, types of punches/kicks missed & thrown, pursuit angles, distance, ring location etc. Additionally coaches can see combinations that landed on the fighter and what landed on their opponent via the software applications of the system 100 and take that information to optimize training by linking together punch and or kick combinations that their upcoming opponent may be susceptible to and avoid fight combinations their fighter may be susceptible to.

While the major consumer of the data may be the gyms which will include the user, their trainers, physicians, and nutritionists, the data generated by the system 100 may be made available for medical research teams who want to study potential long term impacts associated with activities, such as fighting. One such group would be neurocognitive experts wanting to understand how rotational forces impact fighters over the long term. Such professionals could receive the data the wearable devices 115, 125 produce when they are placed on the skull. Essentially placing this device on the skull throughout a user's career could provide research groups with real-time data that is currently unavailable to them and could help aide them in helping a user decide when it is best to walk away from the sport and to facilitate concussion detection and awareness. The wearable devices 115, 125 on board sensors will have the ability through the user's sweat to detect chemical properties linked to dehydration which will allow the athletes camp to visualize the weight cutting process and ensure the athlete is healthy and safe during the process. Additionally organizations, athletic commissions, doctors and others involved with user safety will have the ability to monitor a user's hydration levels during training camp through to their weight cutting process and on through the athletes live event.

The wearable devices' 115, 125 ability to transfer data makes it a given to provide real-time data to broadcast and streaming networks with events online, via software applications and/or via social media to apply to on-screen graphics as well as delivering to their play-by-play and analysis people to provide such data to television audiences. Via the wearable devices' 115, 125 wireless connectivity, those in print and social media may also receive real-time data to update their social media feeds or the data can be added to an article being worked on. An audience viewing a monitored user may receive real-time data via the wireless connectivity. For example, if a knockout occurs in a boxing match, fans will have the speed of the punch as well as the force (fighting's version of how long a home run flew in baseball) available to them in real-time. The same goes for punch and kick statistics during a match, instead of a fan having to search online, all data may be transmitted immediately to their personal computing device. For fighter safety, ringside doctors can receive biometric conditions on a tablet, smart watch, smart glasses, augmented reality devices, virtual reality devices, and/or phone that will alert them of any abnormalities or issues that may require them to stop the fight. Given the wearable devices' 115, 125 adhesive form factor and being able to place the wearable devices' 115, 125 on the head behind the ear where it has been deemed illegal to hit, physicians can create a force threshold by which they may be able to monitor and detect when a fight needs to be stopped due to potential head trauma.

From a fans perspective, fans can take advantage of augmented reality while utilizing the data derived from the sensor devices (e.g. wearable device 115, 125) that each athlete is wearing. Fans at events can position their phone, tablet and/or computing device towards the athletes, in this case pointing the device screen (e.g. first user device 102) towards the field of play or at the television screen and having the ability to view the athletes heart rate, exhaustion level, punches and kicks landed/missed, average power/ speed top power landed etc. as it will appear on their devices' screens as if the data is floating right next to each of the fighters or the user can point their devices toward the ring as each fighter is sitting on their stool in between rounds to see the previous rounds statistics in the ring hovering around each fighter. The platform provided by the system 100 may also give fans, on their devices, replays with data or the same can be reproduced on the big screen in arena or stadium. The same possibilities exist for pointing the devices at the television screen. Fans of sporting events will also be able to view events that utilize the system's 100 platform and data stream through virtual reality headsets and virtual reality broadcasts in real-time. Also, the system 100 may incorporate smart glass compatibility, which will allow a fan or user using smart glasses to view in-game or in-fight statistics and see analytics via the heads-up-displays within the smart glasses. All of the data can be transferred to the smart glasses in real-time and the fans may also be privy to historical data. The same possibilities exist with augmented reality glasses and other augmented reality devices, but the data may appear to be on the playing field or actually in the arena. In certain embodiments, coaches may have access to that same information, including biometrics in real-time as they record a training session.

One other use of the system 100 would be to replace the outdated use of CompuBox, which fans, professional fighters and experts alike find fallacy in. CompuBox involves gentlemen tapping buttons that represent the different types of punches that can be thrown (mind you there are no kick types being monitored), in addition to totaling the number of and types of punches thrown. Notably, the statistic that CompuBox calculates, which is highly inaccurate, is the number of punches landed. Such a technology is an outdated technology that is prone to user error and has a direct impact on who the viewing public believe won a match as it is the only source of data currently given to the viewing public, broadcast networks, and/or editorials. So another source of information the flexible wearable devices 115, 125 would be able to provide besides describing the types of punches, elbows, knees, and kicks thrown and the punches, elbows, knees, and kicks that landed and missed, is being able to come up with a metric using artificial intelligence to determine punch or other body strike quality, punch or other body strike effectiveness, how clean a punch or other body strike is, which may be judging criteria to determine a winner, but is not easy to determine with the human eye. The flexible wearable devices 115, 125 (in certain embodiments may be flexible epidermal electronic devices) will be able to detect where a punch landed and see the quality of the punch by determining if it was partially blocked or where it landed based on tracking the opponent's glove and body location. The sensors embedded within the wearable devices 115, 125 (e.g. epidermal electronic devices) have the ability to relay to the system 100 and/or software applications exactly where punches landed by identifying the density of the area or object they are hitting. As a result, this could also play into the wearable devices 115, 125 notifying the system 100 of the activity that the user is engaging in, if the user is hitting bag or speed bag the sensors can detect that and help the system 100 properly record the activity. Having accumulated historical data on each athlete, the system 100 will be able to determine the percentage of their total force that each individual is using in each of their strikes. The system 100 may be adapted for use in recreational gyms where consumers are using combat sports as a fitness tool, which can give each individual all of the performance and biometric data, along with calories burned and any other pertinent fitness metrics. The devices' function in gyms that utilize combat sports for fitness much like devices work in cycling gyms, such as Orange Theory Fitness™. Finally, gyms will be able to give users the ability to visualize their performance rather than being told they have improved or need to improve in areas. Gyms can contain leaderboards that visually show the users information on technique, speed, force, foot placement, what type of punches and kicks they threw, elbows and knees thrown, what landed, what missed and will show them what they need to work on. Users may also be given their biometric feedback such as heart rate, oxygen level, hydration level and they can compare that against their physical movements. Utilizing the devices and receiving instantaneous and historical feedback also paves the way for online coaching and teaching where a user's progress can be monitored via video and the software applications supported by the system 100. The system 100 can provide visual confirmation of improvements and how hard a user is actually working while performing an activity. The devices may also have the ability to provide users with feedback on performance in regular fitness gyms. The system 100 may also give users technique feedback paired with biometric data when using weighted equipment and performing exercise related movements. CrossFit™ trainers and trainees could utilize the devices flexibility and abilities to be used anywhere on the body to get the most out of training while also seeing how their biometrics parallel their training.

As shown in FIGS. 1-14, a system 100 that includes utilizing flexible wearable devices 115, 125 for the tracking and monitoring of biometric and other data associated with users is disclosed. The system 100 may be configured to support, but is not limited to supporting, data and content services, computing applications and services, cloud computing services, health-monitoring applications and services, internet services, satellite services, telephone services, software as a service (SaaS) applications, mobile applications and services, and any other computing applications and services. The system may include a first user 101, who may utilize a first user device 102 to access data, content, and applications, or to perform a variety of other tasks and functions. As an example, the first user 101 may utilize first user device 102 to access an application (e.g. a browser or a mobile application) executing on the first user device 102 that may be utilized to access web pages, data, and content associated with the system 100. In certain embodiments, the first user 101 may be any type of user that may potentially participate in an activity. For example, the first user 101 may be an individual that is participating in a mixed martial arts match, a sports game, a boxing match, a wrestling match, any type of exercise, any type of game, or any combination thereof. The activities may be any type of activity that involves some type of movement and/or activity by the first user 101.

The first user device 102, which may be utilized by the first user 101 or another user, may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. screen, monitor, graphical user interface, etc.) that may enable the first user 101 to interact with various applications executing on the first user device 102, to interact with various applications executing within the system 100, and to interact with the system 100 itself. In certain embodiments, the first user device 102 may be a computer, a laptop, a tablet device, a phablet, a server, a mobile device, a smartphone, a smart watch, smart-home device, smart glasses, augmented reality devices, virtual reality devices (e.g. headsets), and/or any other type of computing device. Illustratively, the first user device 102 is shown as a mobile device in FIG. 1. The first user device 102 may also include a global positioning system (GPS), which may include a GPS receiver and any other necessary components for enabling GPS functionality, accelerometers, gyroscopes, sensors, and any other componentry suitable for a mobile device.

In addition to the first user 101, the system 100 may include a second user 110, who may utilize a second user device 111 to access data, content, and applications, or to perform a variety of other tasks and functions. The second user 110 may be an individual that is interested in monitoring and/or tracking the first user's 101 performance during one or more activities, the first user's 101 fitness improvements, the first user's 101 health, or any other aspect of the first user 101. For example, the second user 110 may be a trainer, a physician, spectators, or any other individual. Much like the first user 101, the second user 110 may utilize second user device 111 to access an application (e.g. a browser or a mobile application) executing on the second user device 111 that may be utilized to access web pages, data, and content associated with the system 100. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. The second user device 111 may also include an interface 114 (e.g. a screen, a monitor, a graphical user interface, etc.) that may enable the second user 110 to interact with various applications executing on the second user device 111, to interact with various applications executing in the system 100, and to interact with the system 100. In certain embodiments, the second user device 111 may be a computer, a laptop, a tablet device, a phablet, a server, a mobile device, a smartphone, a smart watch, smart-home device, smart glasses, augmented reality devices, virtual reality devices (e.g. headsets), and/or any other type of computing device. Illustratively, the second user device 111 may be a computing device in FIG. 1. The second user device 111 may also include any of the componentry described for first user device 102.

In certain embodiments, the first user device 102 and the second user device 111 may have any number of software applications and/or application services stored and/or accessible thereon. For example, the first and second user devices 102, 111 may include applications for analyzing, processing, and visualizing biometric data from the sensors 119, 129 and acceleration data from the accelerometers 118, 127, cloud-based applications, search engine applications, health-monitoring applications, biometric applications, database applications, applications for performing mathematics, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 101, 110 to readily interact with the software applications. The software applications and services may also be utilized by the first and second users 101, 110 to interact with any device in the system 100, any network in the system 100, or any combination thereof. For example, the software applications executing on the first and second user devices 102, 111 may be applications for receiving data, applications for storing data, applications for determining and identifying users participating in an activity, applications for receiving demographic and preference information for the users, applications for transforming data, applications for executing mathematical algorithms, applications for generating and transmitting electronic messages, applications for generating and transmitting various types of content, any other type of applications, or a combination thereof. In certain embodiments, the first and second user devices 102, 111 may include associated telephone numbers, internet protocol addresses, device identities, or any other identifiers to uniquely identify the first and second user devices 102, 111 and/or the first and second users 101, 110. In certain embodiments, location information corresponding to the first and second user devices 102, 111 may be obtained based on the internet protocol addresses, by receiving a signal from the first and second user devices 102, 111, or based on profile information corresponding to the first and second user devices 102, 111.

The system 100 may also include a wearable device 115, features of which are shown in FIGS. 1-8. The wearable device 115 may be utilized to obtain biometric measurements of an individual and acceleration data corresponding to limb or body part movements of the individual, such as during performance of an activity. The wearable device 115 may be configured to be flexible and each of the components of the wearable device 115 may be configured to be flexible so as to withstand impacts from another object. The wearable device 115 may be configured to include, but is not limited to including, a flexible electronic circuit 116, a microcontroller 117, an accelerometer 118, a sensor 119, a transmitter 120, a plurality of power sources 121, and a covering 122. The flexible electronic circuit 116 may be a ribbon that allows the other components of the wearable device 115 to be electrically connected to each other. The microcontroller 117, the accelerometer 118, the sensor 119, the transmitter 120, and the plurality of power sources 121 may be mounted onto the flexible electronic circuit 116. The microcontroller 117 may include a processor for processing the various data and signals received from the accelerometer 118, the sensor 119, and/or other components of the wearable device 115. The microcontroller 117 may also be configured to include a memory that stores instructions, which are then executable by the processor of the microcontroller 117. The microcontroller 117 may include flexible transistors. The microcontroller 117 may also include any componentry and functionality of a traditional microcontroller.

The accelerometer 118 may be configured to measure acceleration data corresponding to movement of a body part on which the wearable device 115 is attached. For example, the accelerometer 118 may be configured to measure the speed at which a body part moves, a force at which the body part is moved, and/or a force at which the body part contacts another surface or object. The accelerometer 118 may be a capacitive type, a linear differential variable transformer (an accelerometer that tracks the displacement of a ferromagnetic core relative to solenoids to sense linear acceleration), and/or a piezoelectric type, which may be utilized to track punch, body movement, and/or kick counts, speed associated with such movements, and/or force associated with such movements. In certain embodiments, the accelerometer 118 may be a microelectromechanical system (MEMS) device that consists of micro-machined elements. During normal operation, a "shuttle" that is anchored on two sides will accelerate relative to fixed electrodes. This movement will generate an output voltage that can then be analyzed to determine the acceleration of the wearable device 115. The sensor 119 may be any type of sensor that is configured to obtain biometric measurements of an individual. For example, the sensor 119 may be an optical sensor configured to measure an individual's heart rate, a pressure sensor, and/or an electrode for tracking a heart rate. The sensor 119 may also include an oxygen sensor configured to measure the individual's oxygen levels, a blood pressure sensor configured to measure the individual's blood pressure, a hydration sensor (e.g. microneedles or other suitable sensors) configured to measure a level of hydration and/or dehydration of the individual, a stress sensor configure to measure a stress level of the individual, any other type of biometric sensor, or any combination thereof. In certain embodiments, the wearable device 115 may also include an altimeter and/or a magnetometer. The transmitter 120 may be a wireless transmitter, such as a short-range wireless transmitter (e.g. Bluetooth™), which may be configured to transmit data obtained by the sensors and microcontroller 117 of the wearable device 115 to the other components and devices of the system 100, such as first user device 102 and second user device 111. The transmitter 120 may also be a radio frequency transmitter or any other type of transmitter. The power sources 121 may be flexible batteries, such as lithium-ion batteries, a piezoelectric power source, and/or a solar power source. The covering 122 may be a matrix material, which may include a pocket 123 that may be configured to receive the flexible electric circuit 116 and the components attached thereon. The wearable device 115 may attach to body parts of the user by way of an adhesive that is on a bottom surface of the wearable device 115 itself, an adhesive wrist wrap, or by attaching the wearable device 115 to gloves, wrist wraps, or other clothing. Notably, each of the components of the wearable device 115 may be flexible and may be supported by the patch matrix material of the covering 122 so as to withstand impacts experienced by a user wearing the wearable device 115.

With regard to the wearable device 115, engineering analyses were conducted relating to power consumption, composite material stress, and thermal, wiring, and signaling analysis. The components of the wearable device 115 may draw power from a rechargeable power source 121 (e.g. battery), and the battery will be able to sustain the wearable device 115 with at least nine hours of battery life. In addition to this, the proposed wiring configuration for the wearable device 115 is feasible, as each component will receive power from the battery and the ground pins on each component will be connected to ground. In certain embodiments, the wearable devices' 115 patch matrix material was determined to be neoprene or ethylene-vinyl acetate, and the ribbon material of the flexible electronic circuit 116 was determined to be either PEEK or Polyamide due to the materials' high elastic modulus to reduce stress on the wearable device 115 matrix. The signal analyses concluded that these chosen materials will not interfere with the wireless signals emanating from the wearable device 115. In order to track combat statistics, the wearable device 115 will track the first user's 101 heart rate, punch count, and punch speed and/or other body movement metrics. The wearable device 115 will relay the combat statistics from the sensors to a processing unit (e.g. microcontroller 117 or other processors of the system 100. Notably, the system 100 provides a user application for trainers and users to interface with. The electrical components of the wearable device may be provided with power and a mechanism to turn on/off combat statistics tracking in order to conserve power. In order to be used in professional combat environments, the wearable device 115 confirms the identity of the user and attaches to the user to allow for combat statistic tracking to take place. The flexible nature of the wearable device 115 allows it to continue tracking combat statistics in the event of direct impact on the wearable device 115 itself.

The electrical components of the wearable device 115 will produce heat that should be dissipated in order for the electrical components to continue working as well so as not to harm the wearer. The components utilized in the design allow for relatively little heat generation as well as an effective heat dissipation method. The wearable device 115 may be worn by users either during competition, training, and/or their weight cutting process, and, as a result, will encounter a good amount of sweat on the wearable device 115. The wearable device 115 and all of its electrical components may be hydrophobic and can continue operation whether the athlete is swimming or sweating profusely. In order to allow for professional use, the thickness of the design enables use in professional competition. The wearable device 115 is thin enough to non-intrusively fit under tape (e.g. kinesiology tape), gauze, and/or gloves as well. The wearable device 115 fits on the user in a way where the user does not feel uncomfortable. The wearable device 115 is reusable and can be reapplied adhesively to the user over and over again or the device can be disposable for one-time use or one-week use (or other period of time use). The power source 121 for the wearable device 115 is rechargeable as well in order for continued use by professional combat athletes. The electrical components of the wearable device 115 may be configured to be not too rigid. The wearable device 115 may be able move directly with the user's skin due to how thin the wearable device 115 is and how it stretches with the skin. This greatly increases the impacts it is able to withstand. The wearable devices 115 are flexible enough that they can be folded over in every direction, can be bent, twisted, rolled up and the devices will maintain the same exact usability that it had from the beginning of its lifecycle.

In certain embodiments, the thickness of the wearable device 115 will be under 6.35 mm or 5 mm in order to be thin enough to be worn in professional competition as well as be competitive against similar products. The wearable device 115 can withstand a compressive strength of 14,673 N force. The battery life may be configured to last more than 4 hours, which is greater than the length of an average MMA match or championship boxing mach and longer than the average combat sport training session. The wearable device 115 may be configured to be sweat/water resistant or completely hydrophobic in order to continue operating when met with such conditions. The wearable device 115 will be able to transmit combat statistics from one side of the ring to the opposite ring side or scores table. An MMA ring is about 9 m in diameter plus a buffer of 3 m gives a 12 m distance the wearable device 115 must be able to transmit combat statistics in real time. The wearable device 115 has the ability to track heart rate, punch and kick acceleration, utilize an internal power source, and be able to process and store the data. Every time blood is pumped from the heart, blood vessels expand due to the change in pressure and a pulse is generated. When blood flows back to the heart, another pulse occurs. This generates what is known as a photoplethysmography (PPG) signal, which is the superposition of both pulses and heart beat information and can be used to determine the heart rate. When a punch or kick is performed there is multi-axial acceleration until the point of contact which can be measured to determine the acceleration produced by the motion. The output from the sensors may be converted to a digital signal before the data can be processed. Once the data has been processed, the wearable device 115 may either store the data for future retrieval or transmit the data to another device for analysis. The wearable device 115 will also attach or conform to the user's skin and withstand impact during data acquisition. Also, the power source 121 of the device may be rechargeable so as to allow for multiple uses of the product, or, in other configurations, the wearable device 115 may not be rechargeable, such as if it will be disposable. The wearable device 115 may be placed on the inner wrists (for best pulse or heart rate reading) and on the back of the leg above the heel preferably for combat sports. Nevertheless, usage is completely up to the user as they can place the device anywhere on the user's body and garner the data from that specific area, even being able to place the device on their chest to get the most accurate heart rate reading. During combat these devices may be covered with tape, hand wraps and gauze that fighters wrap around their hands, shin guards around the legs, and ankle wraps that cover the ankle down to the feet.

Referring to FIGS. 5-8, in order for the wearable device 115 to be useable in professional combat sports, the device must be able to withstand high impact that will cause deformation and deflection of the material based on its elastic properties. To confirm that this primary objective of the design can be satisfied, an analysis of the deformation and deflection of the device material was performed. A strain analysis concerning change in the thickness dimension (t) of the patch and a bending deflection analysis were used to predict patch behavior. These two analyses were then used to find relationships between the elastic modulus of the patch, a material property, and the patch deformation and deflection. Therefore, material selection could be strategically performed to control the mechanical properties of the device under load. To evaluate the deformation that would be observed as a change in thickness upon impact, the wearable device 115 was assumed to be a beam, with a thickness (t), cross sectional area (A), and constant material elastic modulus. These values are labeled in the Figures, and were used to perform a deformation analysis to find the thickness change (δt). Additionally, in order to perform this analysis a maximum impact loading condition was expected, using maximum kick force data collected from professional MMA fighters with a factor of safety of 1.2 assumed. Using the fundamental stress strain relationship, shown below in Equation 1, a general equation was derived for the change in wearable device 115 thickness as a function of known variables, shown in Equation 2.

$$E = \frac{\sigma}{\varepsilon} \qquad (1)$$

$$\delta t = \frac{Pt}{EA} \qquad (2)$$

Where:
E=Elastic Modulus of Material (Pa)
σ=Stress on Cross Sectional Area A (Pa)
ε=Strain on Patch
P=Maximum Load (N)

A=Patch Cross Sectional Area (m²)
δt=Change in Thickness of Patch (m)
t=Thickness of Patch (m)

To evaluate the deflection of the wearable device 115 when put under similar loading conditions as the deformation analysis, the same max load[12] was used for the bending deflection analysis. The wearable device 115 (i.e. wearable patch) was assumed to be a beam, with a thickness (t), length (L), and constant material elastic modulus. These values are labeled in the Figures, and were used to find the max deflection of the wearable device 115 ($\delta_{MAX}$) under worst case loading conditions. The load was assumed to be a point source acting on the center of the patch while the ends of the patch remained fixed. Using the beam bending equation, shown in Equation 3, a solution for the maximum deflection due to this type of loading, shown in Equation 4 was used for the analysis.

$$EI\frac{d^4\delta(x)}{dx^4} = P(x) \tag{3}$$

$$\delta_{MAX} = \frac{PL^3}{48EI} \tag{4}$$

Where:
E=Elastic Modulus of Material (Pa)
I=Moment of Inertia of the Beam About the x-axis (kg-m²)
P=Maximum Load (N)
δ=Deflection of the Patch (m)
$\delta_{MAX}$=Maximum Deflection of the Patch (m)
L=Length of Patch (m)

In order for the wearable device 115 to be useable in professional combat sports, the wearable device 115 must be able to withstand high impact per the design specifications. To confirm that this primary objective of the design can be satisfied, an analysis of the stresses on the wearable device 115 must be performed. Since the design will have a flexible ribbon for electrical component mounting and a matrix that will protect the electrical components, a composite material analysis is necessary for a holistic understanding of the stress distribution of these two materials. The wearable device 115 is assumed to be a beam, with a cross width (b), thickness ($t_1+t_2$), and length (L), corresponding to the actual width and length of the wearable device 115 respectively. Using the Transformed Section Method, shown in the FIG. 7, the relationship between the Young's modulus of the two different materials can be factored into the stress analysis through a Transformation Factor (n), found using Equation 5 below. This factor changes the width of one material, allowing for an assumption of material uniformity during future analysis.

$$n = \frac{E_2}{E_1} \tag{5}$$

Where:
n=Transformation Factor
$E_n$=Elastic Modulus of Material n (GPa)
d=Width of Patch (m)
t1=Thickness of Ribbon Material (m)
t2=Thickness of Matrix Material (m)
$\overline{y}_n$=Centroid of Material n (m)
$\overline{y}_c$=Centroid/Neutral Axis of Composite Beam (m)

After composite beam transformation, a bending stress analysis was performed using a bending moment calculated using Equation 6. This equation assumes that the wearable device 115 is again a beam with the aforementioned dimensions, fixed at both ends, and has a point force applied at the center of the beam. These assumptions were made to model the worst case scenario for bending of the wearable device 115. The maximum load for this calculation was based on kick force data with a factor of safety of 1.2, collected from the strongest MMA impact ever recorded.

$$M = \frac{PL}{4} \tag{6}$$

Where:
M=Bending Moment of Beam due to Point Load (N-m)
P=Maximum Force of Impact (N)
L=Length of Beam (m)

The stress that each material would experience after applying this bending moment was then calculated using Equation 7 and Equation 8. These two stress values were then used to show how different material selection, which would allow for control for the Transformation Factor, would allow for different stresses in each material.

$$\sigma_{MAX-Ribbon} = -n\frac{My}{I_{na}} \tag{7}$$

$$\sigma_{MAX-Matrix} = -\frac{My}{I_{na}} \tag{8}$$

Where:
M=Bending Moment of Beam due to Point Load (N-m)
y=Location of Maximum Normal Stress (m)
n=Transformation Factor
$I_{na}$=Moment of Inertia of the Beam about the Neutral Axis (kg-m²)
$\sigma_{MAX}$=Bending Stress on the Selected Material (Pa)

The wearable device 115 will have electrical components to be able to perform combat statistics tracking in real time. The wearable device 115 may include a microcontroller, a transmitter, a pulse sensor, and an accelerometer. The design may include three flexible lithium polymer batteries to power the wearable device 115. The electrical components may operate at varying voltages but each voltage can be scaled so meeting current needs are more important. Each component will be assumed to in its operating mode that draws the most current. Dividing the battery capacities by the sum of all the current needs yields about 9 hours of battery life. In order to ensure that neither the first user 101, nor the electrical components will be damaged by heat; an analysis of the thermal load and heat dissipation was performed. A finite differential analysis divides the wearable device 115 into an m×n matrix with evenly spaced nodes and uses this matrix to analyze how the temperature of a given node affects the area surrounding the node as shown in Appendix C. This approach is governed by Equations 7-9 shown below and was used to understand the potential temperature levels of the device.

$$T_{m,n+1}+T_{m,n-1}+T_{m+1,n}+T_{m-1,n}-4T_{m,n}=0 \tag{7}$$

Case 1: Interior Node[21]

$$(2T_{m-1,n} + T_{m,n+1} + T_{m,n-1}) + \frac{2h\Delta x}{k}T_\infty - 2\left(\frac{h\Delta x}{k} + 2\right)T_{m,n} = 0 \quad (8)$$

Case 2: Node at a pane surface with convection[21]

$$(T_{m,n-1} + T_{m-1,n}) + 2\frac{h\Delta x}{k}T_\infty - 2\left(\frac{h\Delta x}{k} + 1\right)T_{m,n} = 0 \quad (9)$$

Case 3: Node at an external corner with convection[21]
Where:
T=temperature [K]
m=position along x-axis
n=position along y-axis
∞=ambient conditions
h=convective coefficient $$\left[\frac{W}{m^2 * K}\right]$$

k=thermal conductivity $$\left[\frac{W}{m * K}\right]$$

A cross section of the device was divided into equal quadrants and analyzed using a script, to produce contour plots of the given conditions. The device may be assumed to be a flat plate with constant properties throughout, have heat transfer in only two dimensions, and heat generation at a single point in the center of the plate.

Figure 8:
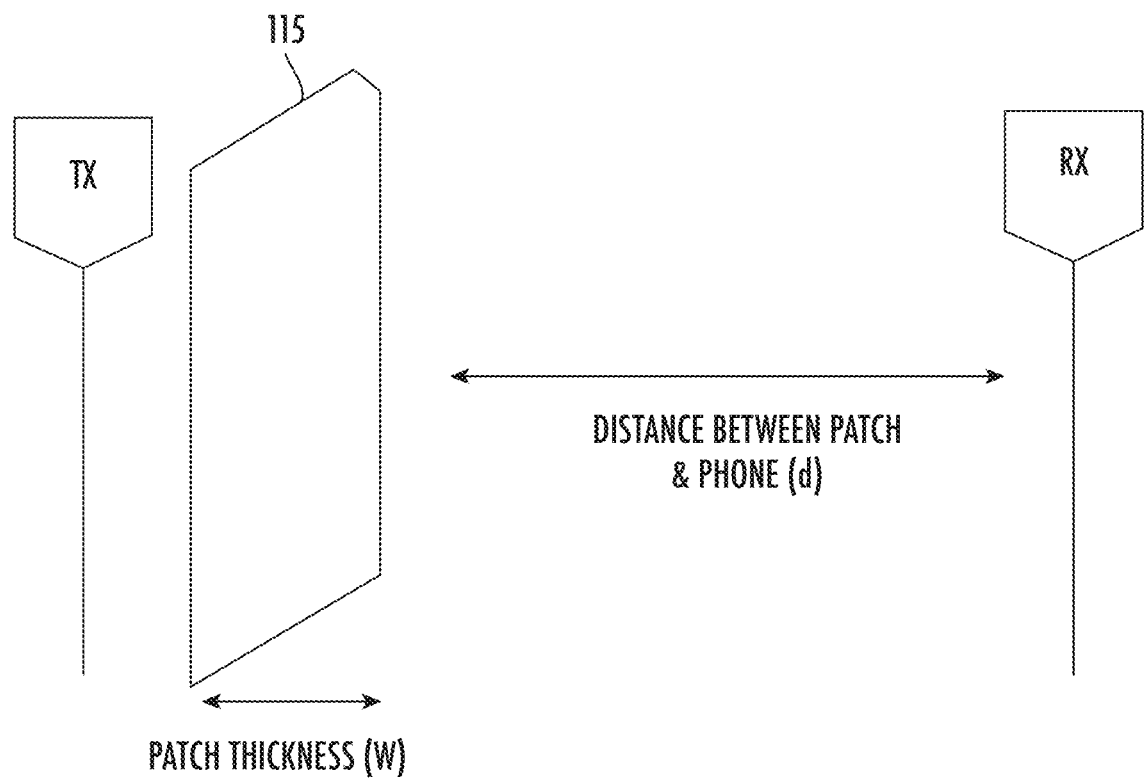
FIG. 8 is a schematic diagram illustrating signal transmission between a flexible wearable device and components of the system of FIG. 1.
Figure 9:
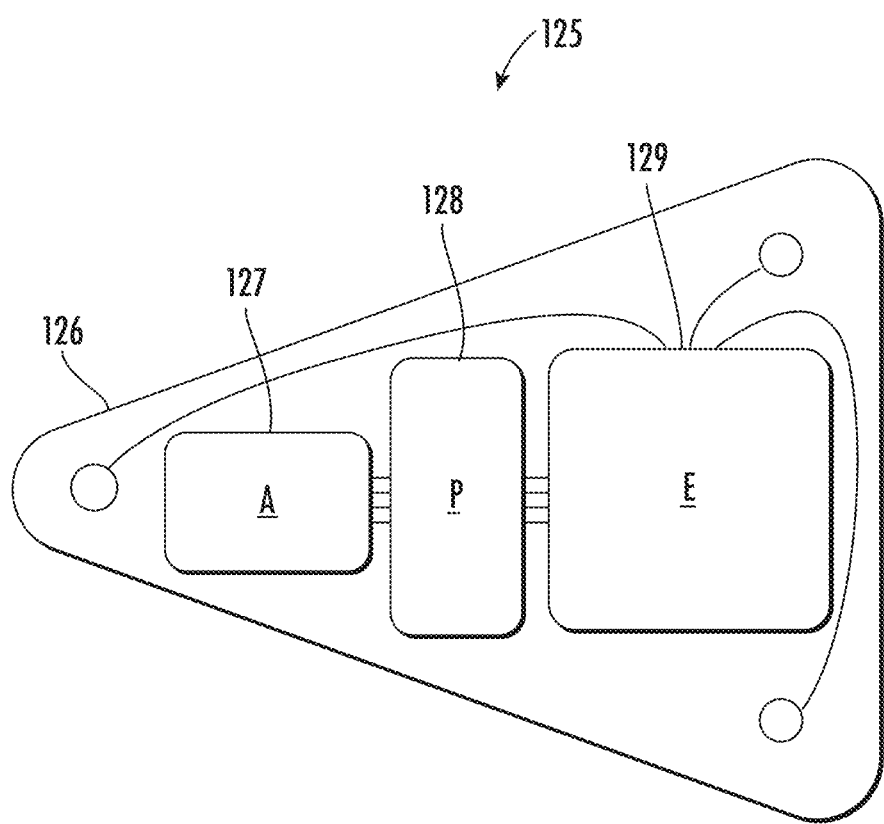
FIG. 9 is a schematic diagram illustrating a top view of another embodiment of a flexible wearable device for use with the system of FIG. 1.
Figure 10:
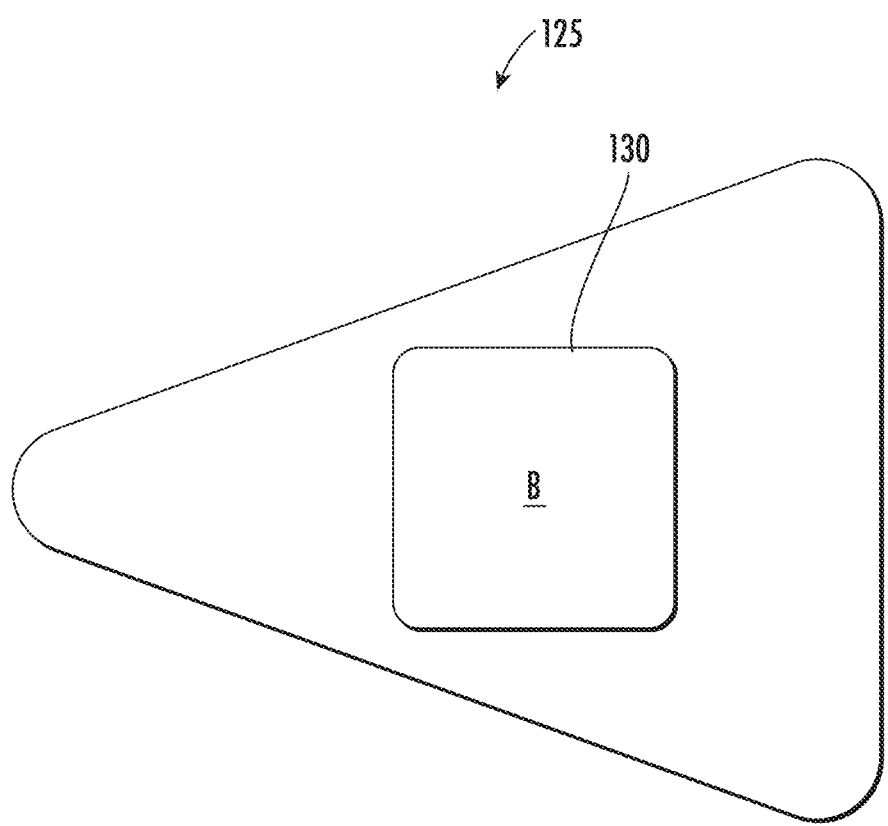
FIG. 10 is a schematic diagram illustrating a bottom view of the embodiment of the flexible wearable device of FIG. 9.

Referring now also to FIG. 8, wearable device 115 may include a transmitter (e.g. transmitter 120) embedded within the wearable device 115, which will be transmitting data to a first user device 102, such as smartphone. The analysis consideration for the signal uplink will include the medium it travels through which includes but is not limited to the material of the patch and free space, and the power transmission characteristics of the transmitting antennae (on the patch) and that of the receiving antennae (on the smartphone). The following information is required about the transmitter (TX), Receiver (RX) and the material to be able to estimate the received power:
 α—Attenuation Coefficient of Patch Material (dB/MHz-mm)
 w—Thickness of Patch Material (mm)
 $P_t$—Power transmitted by transmitter (dBm)
 $D_t$—Isotropic directivity of transmitter (dBi)
 d—Distance between patch and smartphone (m)
 λ—Wavelength of transmitted frequency (m)
 f—Transmitted Frequency in Hz To calculate the received power ($P_r$) at a receiving terminal given a Free Path, the Friis Transmission Equation is used, which is as follows:

$$P_r = P_t + D_t + 20\log_{10}\left(\frac{\lambda}{4\pi d}\right) \quad (10)$$

The post attenuated power is then calculated, using Equation 11 below, by taking the value of received power ($P_r$) given free space and then using the know ratio of attenuation to find the post attenuated power (final received power) $P_a$.

$$20\log_{10}\left(\frac{P_r}{P_a}\right) = \alpha f w \quad (11)$$

The calculated value of $P_a$ is then compared against the receiving sensitivity of the smartphone antennae.

After performing the stress/strain analysis of the patch cross section, a key result was obtained concerning the change in the patch thickness. Ultimately, this analysis helps make the patch useable and impact resistant in professional combat sports. This deformation analysis was performed to help evaluate how a change in patch thickness can be controlled through material selection. Equation 12 below, shows a generalized function for the maximum change in patch thickness obtained through the analysis. Based on the known patch dimensions per the specification sheet, the maximum change in thickness is only a function of the elastic modulus of the patch, a material property.

$$\delta t = \frac{32,103(N/m)}{E} \quad (12)$$

Where:
 δt=Change in Thickness of Patch (m)
 E=Elastic Modulus of Material (Pa)

Initial matrix material selection, shown below in Table 15, demonstrates how different material selection will impact the device behavior under load. Three matrix materials with known elastic moduli were selected to demonstrate the effect of material selection on change in thickness under load. Due to the fact that the matrix has a low modulus value, the resulting thickness changes were large.

TABLE 15

Various Matrix Material Resultant Thickness Changes

| Material | Elastic Modulus (GPa) | Thickness Change (mm) |
|---|---|---|
| Neoprene | 0.0007-0.002 | 16-45 |
| Silicone Elastomers | 0.005-0.02 | 1.6-6.4 |
| Ethylene-Vinyl Acetate | 0.01-0.04 | 0.8-3.2 |

From Table 15 above, it is clear that as the modulus is increased, the change in thickness of the patch under loading will dramatically decrease. One key observation is that a matrix material with low elastic modulus will allow for flexibility of the device, which is a key customer requirement. However, this analysis shows that device flexibility compromises the electrical components in the device as the matrix material will easily compress, causing stress on the ribbon. Therefore, the material will have to be selected strategically to allow for flexibility while still providing electrical component protection under loading. This can also be controlled by changing the modulus of the matrix through the addition of a matrix material that would increase the overall matrix modulus and provide an increase in patch compressive strength.

The bending deflection analysis will help make the patch useable and impact resistant in professional combat sports. This deformation analysis was performed to help evaluate how change in patch deflection under load can be controlled through material selection. Using known patch dimensions per the specification sheet, a relationship was identified between the elastic modulus and the maximum patch deflection, seen below in Equation 13.

$$\delta_{MAX} = \frac{83,129\left(\frac{kN}{m}\right)}{E} \qquad (13)$$

Where:
δ=Max Deflection of Patch (m)
E=Elastic Modulus of Material (kPa)

Initial ribbon material selection, shown below in Table 16, demonstrates how different material selection will impact the device behavior under load. Two ribbon materials with known elastic moduli were selected to demonstrate the effect of material selection on deflection of the ribbon. The ribbon has a high modulus value when compared to the matrix material. However, it was used in this analysis as the ribbons primary function is to house the electrical components, so a large ribbon deflection would directly impact electrical component functionality under loading.

TABLE 16

Various Ribbon Material Resultant Maximum Deflections

| Material | Elastic Modulus (GPa) | Max Deflection (mm) |
|---|---|---|
| PEEK | 3.6 | 23 |
| Polyamide | 2.4 | 33 |

From Table 16 above, it is clear that as the modulus is increased, the deflection of the patch under loading will decrease. One key observation is that a matrix material with low elastic modulus will allow for flexibility of the device, which is a key customer requirement. However, this analysis shows that device flexibility compromises the electrical components in the device as the ribbon material will deflect, causing bending stress on the components. Therefore, the ribbon material will have to be selected strategically to allow for flexibility while still providing electrical component rigidity support under loading. This can also be controlled by changing the overall modulus of the device to provide support for the electrical components. Similar to the thickness change analysis, the addition of a matrix material that would increase the matrix modulus would increase device total modulus and allow for decreased bending deflection.

After performing the stress analysis of a composite transformed patch cross section, several key results were obtained. This analysis was performed to help evaluate what stresses each material in the patch will experience and how this can be controlled through material selection. Ultimately, this analysis will be useable and impact resistant in professional combat sports. Equation 14 and Equation 15 below, show a generalized function for the maximum stress in both the ribbon and matrix respectively and were obtained through the Transformed Section method.

$$\sigma_{MAX-Ribbon} = \frac{0.69875 * n}{5.71 \times 10^{-7} n + 7.94 \times 10^{-10}} \qquad (14)$$

$$\sigma_{MAX-Matrix} = \frac{0.69875}{5.71 \times 10^{-7} n + 7.94 \times 10^{-10}} \qquad (15)$$

Where:
n=Transformation Factor
$\sigma_{MAX}$=Bending Stress on the Selected Material (Pa)

These two equations are only dependent upon the value of the Transformation Factor (n) which comes directly from the elastic moduli of the selected materials. Therefore, this function allows for the stress that each of the materials experiences to be controlled through material selection. Initial material selection, shown below in Table 17, demonstrates how different material selection and combinations for the matrix and ribbon material will impact the device behavior under load. Two matrix materials with low elastic modulus were selected (Neoprene and Ethylene-Vinyl Acetate) and combined with two different ribbon materials which typically have higher elastic moduli (PEEK and Polyamide). Due to the fact that the matrix has a significantly lower modulus than the ribbon, the resulting Transformation Factor values tended to be low, resulting in a large stress on the matrix and a low stress experienced by the ribbon.

TABLE 17

Comparison of Various Material Combination Resultant Stresses

| Ribbon Material | Matrix Material | n | $\sigma_{ribbon}$ (kPa) | $\sigma_{matrix}$ (kPa) |
|---|---|---|---|---|
| PEEK | Neoprene | $5.55 \times 10^{-4}$ | 349 | 628992 |
| PEEK | Ethylene-Vinyl Acetate | 0.011 | 1086 | 98763 |
| Polyamide | Neoprene | $8.33 \times 10^{-4}$ | 458 | 550352 |
| Polyamide | Ethylene-Vinyl Acetate | 0.0167 | 1130 | 67645 |

One key result from this analysis is that the stress in the ribbon and the stress in the matrix material are inversely related to the Transformation Factor (n). This means that as the matrix material becomes stiffer the ribbon will experience less stress and the matrix will experience more stress. Conversely, if the ribbon material is stiffer then the matrix material will experience less stress and the matrix will experience more. This relationship however is not a one-to-one tradeoff. The analysis shows that increasing n will result in a small increase in the stress on the ribbon and a large decrease in the stress on the matrix. Therefore, ideally the matrix would have a high modulus of elasticity to reduce stress on the matrix significantly, with a very minor increase in stress on the ribbon. However, during design of this device stress on the ribbon should be kept as low as possible to reduce stress on the electrical components, making this tradeoff a consideration for the allowable stresses on the ribbon.

In addition, another key result from this analysis is that the increase in the overall stress resistance of the device can be achieved by adding in a supporting mesh into the matrix material. This will result in a decreased device flexibility due to the addition of a stiff material, but will take some of the stress from the ribbon material. The addition of this mesh will result in a reduction in the overall elastic modulus of the matrix, which is typically low, resulting in high stress on the ribbon and electrical components. The tradeoff between this increased complexity during device manufacture and the benefits of this mesh will be further evaluated later in the analysis of the device.

Power analysis needs to be done to determine the battery life for the Wearable device 115. By examining the battery capacity and current needs for each electrical component, a good indication of battery life can be found. Table 18 below shows the maximum current draw for each electrical component of the Wearable device 115.

TABLE 18

Current Needs for Wearable device 115 Components

| Component | Current Draw (mA) |
|---|---|
| Microcontroller | 0.1 |
| Accelerometer | 0.25 |
| Bluetooth | 27 |
| Pulse Sensor | 4 |
| Lithium Polymer Battery | 100 mAH |

The maximum current draw for all the components combined:

31.35 mA=0.1 mA+0.25 mA+27 mA+4 mA

Placing the three batteries in parallel will yield a total battery capacity of:

300 mAH=100 mAH·3

Dividing battery capacity by current draw will yield:

9.56 H=300 mAH÷31.35 mA

This will leave the wearable device 115 with about 9 hours of battery life. This is well above the battery life specification of greater than 2 hours. It may be advantageous to remove one or two batteries from the design as the battery life specification will still be met as well as the design will get smaller. However, having battery life well over the specification may be convenient for the users as they would not have to charge the device as frequently.

After performing the thermal analysis of the cross section, an important observation was made. This analysis was performed to help evaluate which matrix material will best dissipate heat to ensure that it remains comfortable and within tolerable levels for the electronics. The heat generation of each component, shown in Table 19, was determined using Equation 16 below and the largest of these values was used for analysis purposes.

TABLE 19

Heat Generation for Wearable device 115 Components

| Component | Power [W]$_{Assuming\ 5V}$ | Area [m$^2$] | Heat Generation$_m^{2W}$ |
|---|---|---|---|
| Accelerometer | 0.0005 | 4 × 10$^{-6}$ | 125 |
| Bluetooth Transmitter | 0.00125 | 1.5 × 10$^{-4}$ | 8.33 |
| Heart-rate Sensor | 0.135 | 5.03 × 10$^{-4}$ | 268 |
| Microcontroller | 0.020 | 2.5 × 10$^{-5}$ | 800 |

$$\text{Heat Generation} = \frac{\text{Power}}{\text{Area}} \quad (16)$$

This analysis assumes constant convective coefficient of skin [24] and is therefore only dependent on the value of thermal conductivity (k), which is a property of the selected material. This allows for heat levels of the device to be influenced through material selections. Initial material selection, shown in Table 21, demonstrates how different matrix material selection will impact the device temperature levels. The two matrix materials, introduced earlier (Neoprene and Ethylene-Vinyl Acetate), were selected.

TABLE 20

Theoretical Maximum Temperature of Device

| Matrix Material | k$_{m*K}^W$ | Max Temperature [° C.] |
|---|---|---|
| Neoprene | 0.19 | 24.65 |
| Ethylene-Vinyl Acetate | 0.34 | 24.05 |

One key result from this analysis is that the temperature is inversely related to the thermal conductivity of the material. This means that matrix materials with higher thermal conductivity values will allow for more heat dissipation and result in lower temperatures across the device.

For the initial design of the patch, PEEK and Polyamide were considered for the Patch Ribbon Material.

TABLE 21

Attenuation Coefficient of Smart Patch Ribbon Materials [1]

| Material | Attenuation Coefficient (α) dB/mm-MHz | Attenuation - 3.5 mm * 2483.5 MHz |
|---|---|---|
| PEEK | 1.32127e−5 | 0.114848092 dB |
| Electrical Grade Polyamide-Imide | 1.470588e−5 | 0.127827185 dB |

The following characteristics were then determined based on the specification requirements and specification values of the transmitting antennae (BLE-112A) [2] and the receiving antennae (iPhone 5) [3]:

Transmitter Characteristics:
Pt=+3 dBm (BLE-112)
Dt=+2.3 dBi
Frequency (f)=2483.5 MHz
Wavelength (λ)=7.445346e+17
Receiver Characteristics:
Sensitivity=−95.5 dBm (iPhone 5)
Arena Distance (d)=30 ft (9.144 m)

Using Friis Transmission Formula, the pre-attenuated power was calculated to be P$_r$=379.86222 dBm. Using the respective attenuation coefficient for PEEK and Polyamide-Imide, the post-attenuation or final received power was calculated to be 43.6264 dBm for PEEK and 48.5567 dBm for Polyamide-Imide. Both these values are sufficiently larger than −95.5 dBm. Therefore, the receiver should not only be able to receive the required signal correctly given the arena distance, but also receive a clear signal on an order of ~10-15× the required distance (since dB is a log 10 factor of distance).

Figure 11:
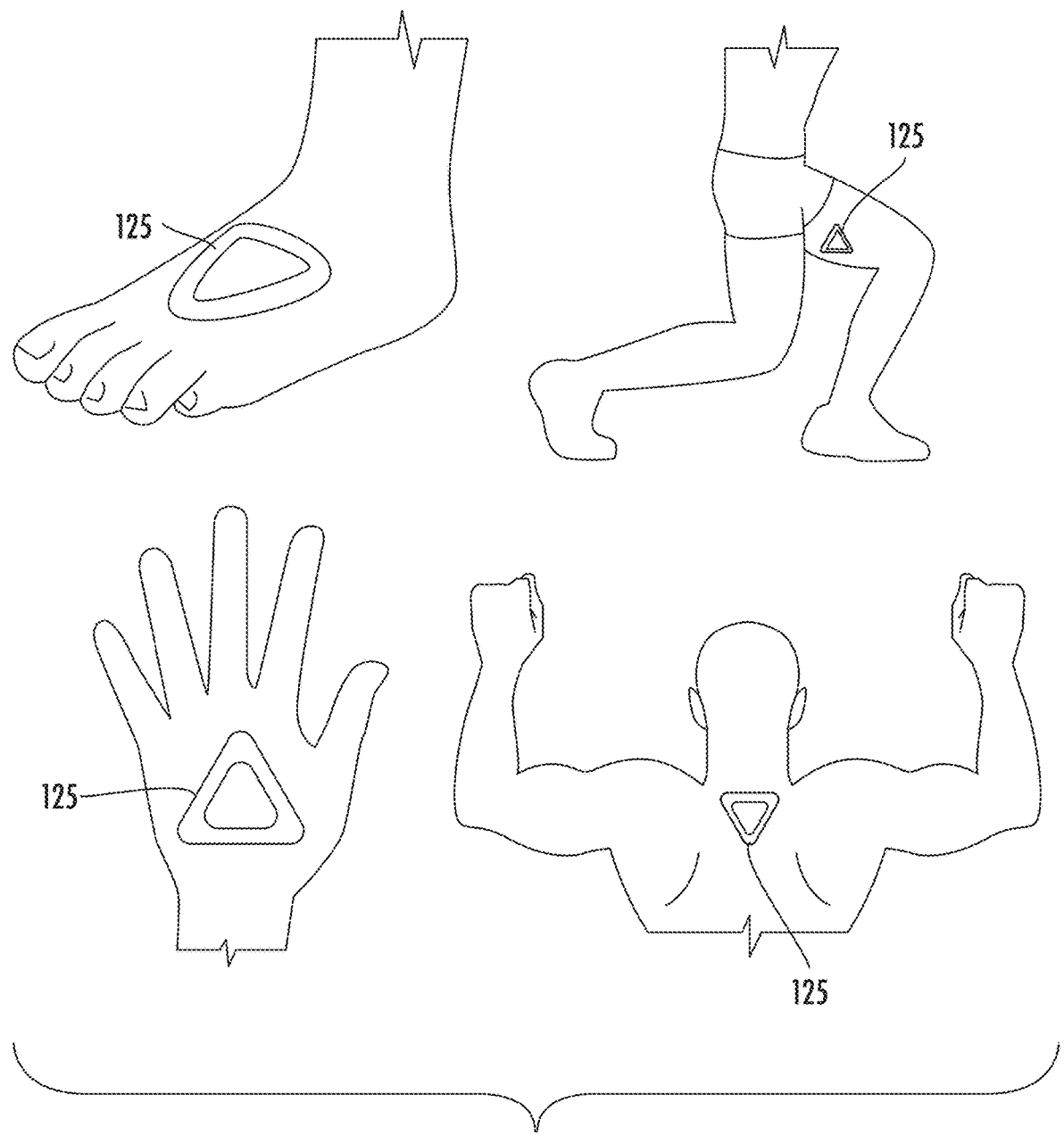
FIG. 11 is a schematic diagram illustrating various locations that the flexible wearable device of FIG. 9 may be placed on a user.

The system 100 may also include another type of wearable device 125, which is illustratively shown as being on the wrist of the first user 101 in FIG. 1 and is shown in detail in FIGS. 9-14. Notably, the wearable device 125 may be placed at any suitable location on the individual. Example locations are shown in FIG. 11 (e.g. top of hand, top of foot, thigh, back, etc.). The wearable device 125 may visually appear like a patch and may include multiple components including, but not limited to, a mounting surface 126, an accelerometer 127, a microcontroller 128, a sensor 129, a power source 130, and a housing tray 1201. The mounting surface 126 may be any suitable mounting surface that may be configured to be made of flexible materials and may be configured to include componentry to enable electrical connections between the components of the wearable device 125. The accelerometer 127 may be configured to measure acceleration data corresponding to movement of a body part on which the wearable device 125 is attached. For example, the accelerometer 127 may be configured to measure the speed at which a body part moves, a force at which the body part is moved, and/or a force at which the body part contacts another surface or object. The microcontroller 128 may include a processor for processing the various data and signals received from the accelerometer 127, the sensor 129, and/or other components of the wearable device 125. The microcontroller 128 may also be configured to include a memory that stores instructions, which are then executable by the processor of the microcontroller 128. Additionally, the microcontroller 128 may also include a transmitter, such as a short-range wireless transmitter or even a long-range wireless transmitter, which may be configured to transmit data received from the sensors and processed by the microcontroller 128 to any other device in the system 100. For example, the transmitter may support Bluetooth™ communications. The microcontroller 128 may also include any componentry and functionality of a traditional microcontroller.

Figure 12:
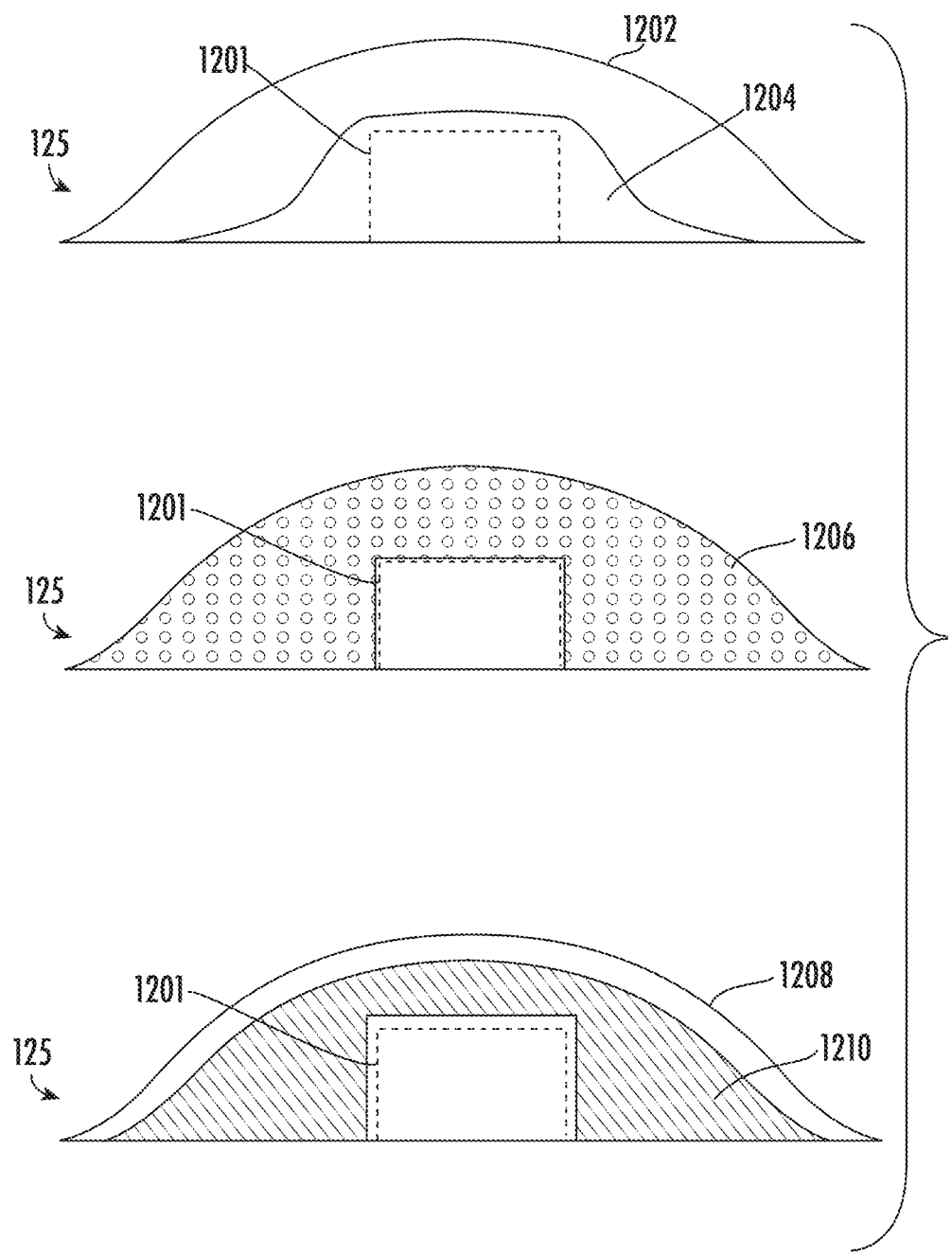
FIG. 12 is a schematic diagram illustrating multiple side views of the flexible wearable device of FIG. 9 for various configurations and materials that may be utilized with the flexible wearable device of FIG. 9.
Figure 13:
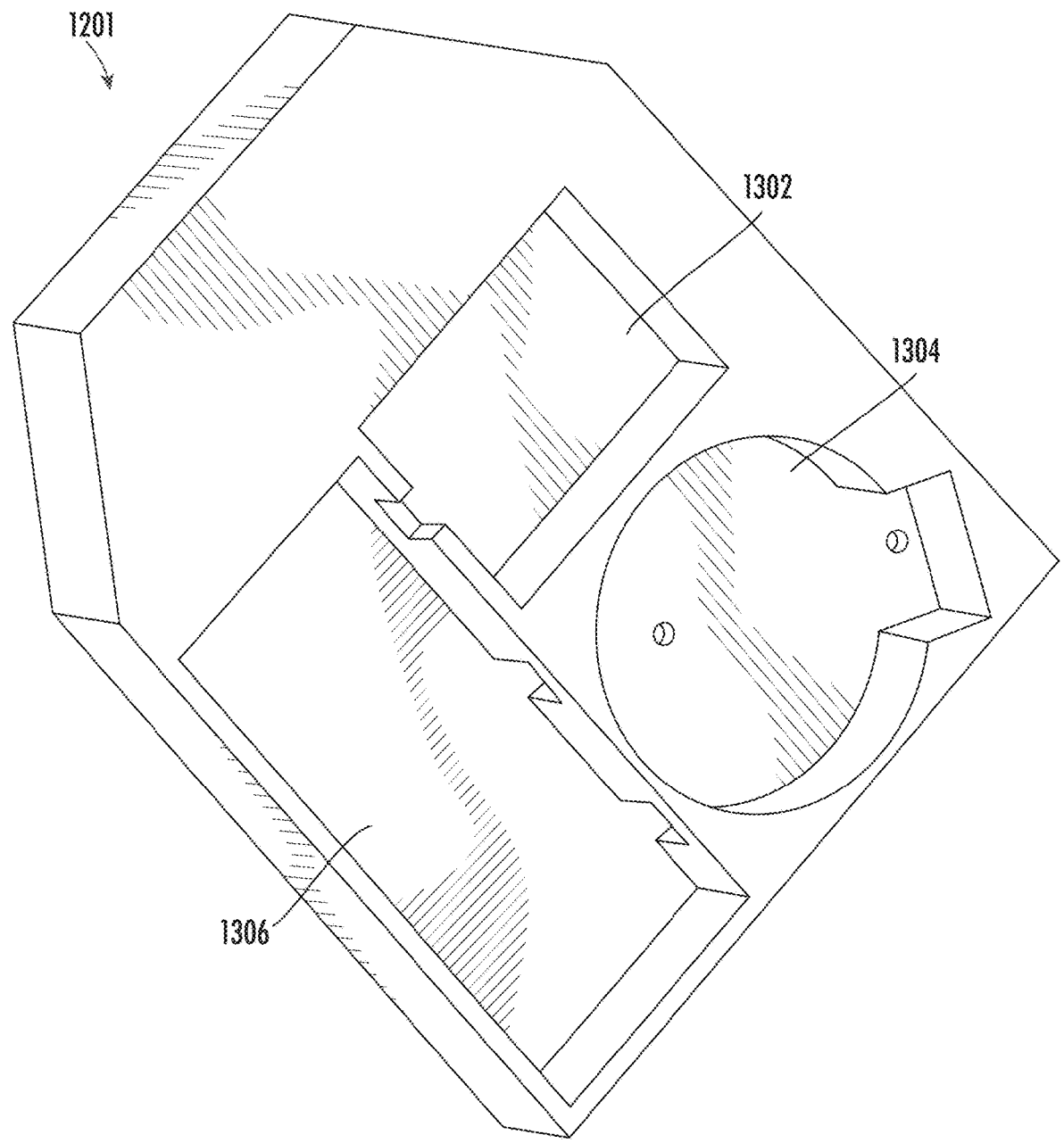
FIG. 13 is a schematic diagram illustrating a top view of a housing tray for housing various components of the flexible wearable device of FIG. 9.
Figure 14:
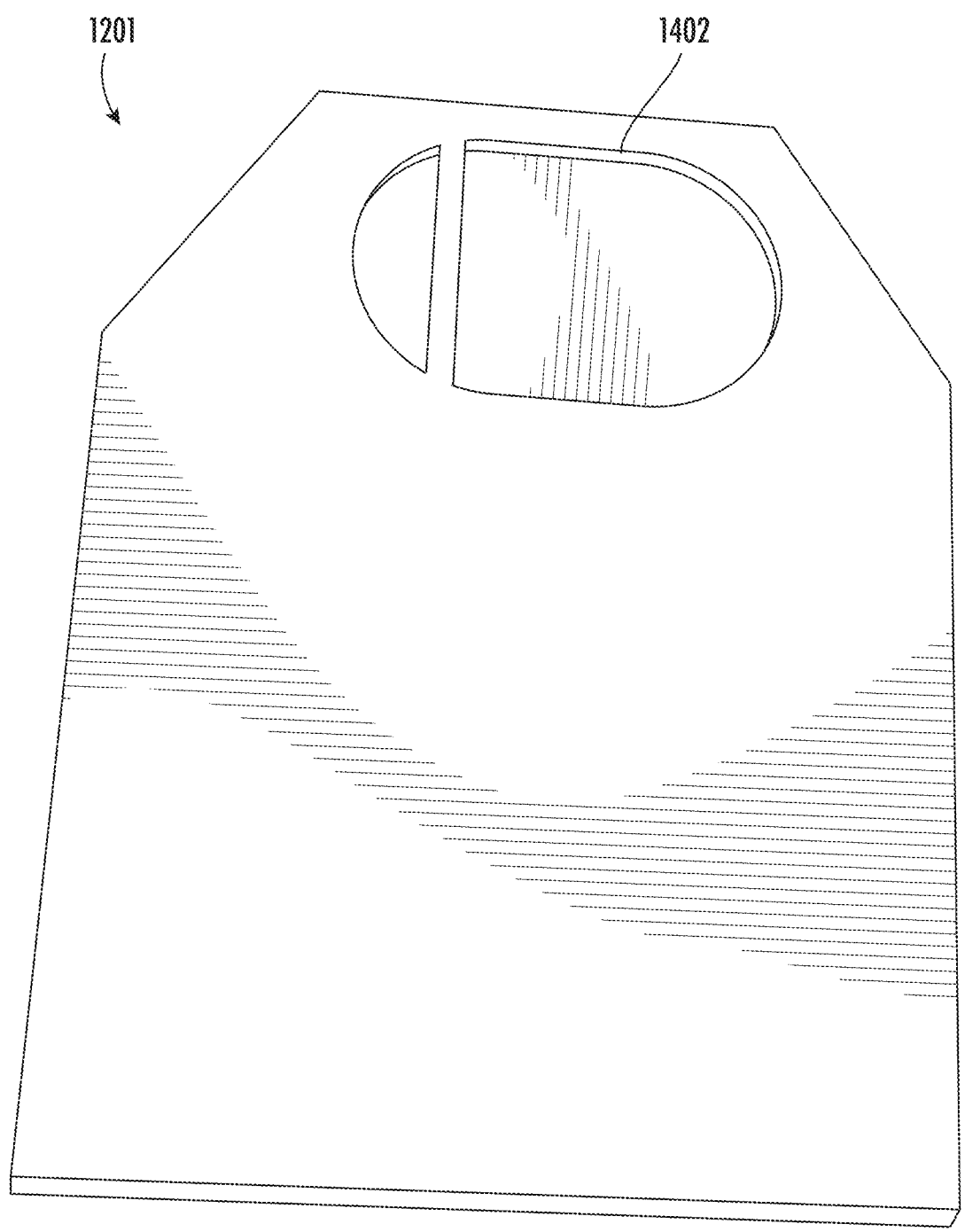
FIG. 14 is a schematic diagram illustrating a bottom view of a housing tray for housing various components of the flexible wearable device of FIG. 9.

The sensor 129 may be any type of sensor that is configured to obtain biometric measurements of an individual. For example, the sensor 129 may be an electrocardiogram circuit configured to measure an individual's heart rate and electrical signals produced by the individual's heart during a cardiac cycle. The sensor 129 may also include an oxygen sensor configured to measure the individual's oxygen levels, a blood pressure sensor configured to measure the individual's blood pressure, a hydration sensor (e.g. microneedles or other suitable sensors) configured to measure a level of hydration and/or dehydration of the individual, a stress sensor configure to measure a stress level of the individual, any other type of biometric sensor, or any combination thereof. In certain embodiments, the system 100 and/or software platform can take advantage of the user wearing any number of wearable devices 115 (e.g. 4 devices that all contain 4 heart-rate sensors). The system 100, for example, may take heart-rate readings, aggregate the data, and then the system 100 can determine a more accurate heart-rate calculation based on the 4 different readings from the different areas of the body that the wearable devices 115 are placed. The power source 130 of the wearable device 125 may be a flexible battery or other power source. Notably, each of the components of the wearable device 125 may be configured to be flexible. The housing tray 1201 of the wearable device 125, as shown in FIGS. 12-14, may be configured to house various components of the wearable device 125. For example, the slot 1304 may be configured to house the power source 130, the slot 1306 may be configured to house the microcontroller 128 and its accompanying transmitter and memory, the slot 1302 may be configured to house the accelerometer 127, and the slot 1402 may house the sensor 129 or any number of sensors 129.

The components of the wearable device 125, including the housing tray 1201, may be protected by various types of coverings, which may comprise matrix material or other suitable flexible materials, which are capable of protecting the componentry of the wearable device 125. In FIG. 12, various example coverings are shown. In the top diagram of FIG. 12, the wearable device 125 has a covering 1202 that covers the housing tray 1201, and has air 1204 serving as insulation between the housing tray 1201 and the covering 1202. In the middle diagram of FIG. 12, the wearable device 125 has a covering 1206 that made of memory foam that serves to protect the housing tray 1201 and components installed thereon, while simultaneously allowing the wearable device 125 to have flexibility. In the bottom diagram of FIG. 12, the wearable device 125 has a covering 1208 and insulation portion 1210 that is made of viscoelastic plastic sorbothane, which allows the wearable device 125 to be flexible.

Notably, multiple wearable devices 125 may be worn by the first user 101 during an activity and the wearable devices 125 may be attached to the body parts of the first user 101 via an adhesive placed on the underside of the covering of the wearable device 125. In doing so, data corresponding to each body part to which a wearable device 125 is attached may be obtained and tracked in real-time, such as during training or during a competitive match. In certain embodiments, the wearable devices 125 may be utilized in a modular fashion in order to obtain force output information from each limb (or other body part) of the first user 101 or other individual. In certain embodiments, a primary wearable device 125 may measure both the heart rate and acceleration data of the first user 101 and peripheral wearable devices 125 positioned on various body parts may be configured to obtain only acceleration data in order to give a force output metric. The wearable device 125, in conjunction with the functionality provided by the system 100, may be configured to track and/or determine the first user's 101 heart rate, heart rate variability, rate of perceived exertion, cardiac index, heart rate to rate of perceived exertion ratio, and force output. These metrics are further discussed in the explanation of method 1600, which is described later in this disclosure. In certain embodiments, the wearable device 125 may be configured to transmit data and information obtained from the components of the wearable device 125 to any external device of the system 100 and/or a software application. The data and information may be processed and filtered by the devices and applications in the system 100. The data and information may be rendered via a user-friendly graphical user interface. Health trends for the first user 101 over time, historical and baseline data for the first user 101, fatigue levels of the first user 101, performance improvements of the individual, and/or and other visualization of data may be rendered and displayed, such as on first and second user devices 102, 111. In further embodiments, the wearable device 125 may be configured to include sensors that measure the breath of the first user 101 to analyze a fatigue level of the first user 101. Faster and shorter breaths may indicate fatigue, whereas long and slow breaths may indicate that the first user 101 is not fatigued and is performing well. In certain embodiments, the wearable device 125 may be incorporated into clothing and fabrics worn by the first user 101 during an activity so as to obtain biometric measurements and performance data.

The system 100 may also include a communications network 135. The communications network 135 of the system 100 may be configured to link each of the devices in the system 100 to one another. For example, the communications network 135 may be utilized by the first user device 102 to connect with other devices within or outside communications network 135, such as, but not limited to, wearable device 115, wearable device 125, second user device 111, the servers 140, 150, 160, and database 155. Additionally, the communications network 135 may be configured to transmit, generate, and receive any information and data traversing the system 100. In certain embodiments, the communications network 135 may include any number of servers, databases, or other componentry, and may be controlled by a service provider. The communications network 135 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. Illustratively, server 140 and server 150 are shown as being included within communications network 135.

Notably, the functionality of the system 100 may be supported and executed by using any combination of the servers 140, 150, and 160. The servers 140, and 150 may reside in communications network 135, however, in certain embodiments, the servers 140, 150 may reside outside communications network 135. The servers 140, and 150 may be utilized to perform the various operations and functions provided by the system 100, such as those requested by applications executing on the first and second user devices 102, 111 and/or even the wearable devices 115, 125. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 150 may include a memory 151 that includes instructions, and a processor 152 that executes the instructions from the memory 151 to perform the various operations that are performed by the server 150. In certain embodiments, the servers 140, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 150 may be communicatively linked to the communications network 135, any network, any device in the system 100, or any combination thereof.

The database 155 of the system 100 may be utilized to store and relay information that traverses the system 100, cache information and/or content that traverses the system 100, store data about each of the devices in the system 100, and perform any other typical functions of a database. In certain embodiments, the database 155 may store the output from any operation performed by the system 100, operations performed and output generated by the wearable device 115, 125, or any combination thereof. For example, the database 155 may store biometric measurements obtained from the sensors 119, 129, acceleration and force data from the accelerometers 118, 127, data from the microcontrollers 117, 128, any other data traversing the system 100, or any combination thereof. In certain embodiments, the database 155 may be connected to or reside within the communications network 135, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operations associated with the database 155. In certain embodiments, the database 155 may be connected to the wearable devices 115, 125, the servers 140, 150, 160, the first user device 102, the second user device 111, any devices in the system 100, any other device, any network, or any combination thereof.

The database 155 may also store information obtained from the system 100, store information associated with the first and second users 101, 110, store location information for the first and second user devices 102, 111 and/or first and second users 101, 110, store user profiles associated with the first and second users 101, 110, store device profiles associated with any device in the system 100, store communications traversing the system 100, store user preferences, store demographic information for the first and second users 101, 110, store information associated with any device or signal in the system 100, store information relating to usage of applications accessed by the first and second user devices 102, 111, store any information obtained from any of the networks in the system 100, store historical data associated with the first and second users 101, 110, store device characteristics, store information relating to any devices associated with the first and second users 101, 110, or any combination thereof. The user profiles may include any type of information associated with an individual (e.g. first user 101 and/or second user 110), such as, but not limited to, skill set information, punching technique information, kicking technique information, limb movement information, force values associated with limb movements, force values associated with limbs contacting various objects or other individuals, health information (e.g. heart rates, oxygen levels, blood pressure values, heart rate variability values, rate of perceived exertion values, dehydration values, and any other health values), contact information, demographic information, psychographic information, work history information, education information, any attributes of the individual, any other information, or a combination thereof. Device profiles may include any type of information associated with a device, such as, but not limited to, operating system information, hardware specifications, information about each component of the device (e.g. sensors, processors, memories, batteries, etc.), attributes of the device, any other information, or a combination thereof.

The database 155 may store algorithms for determining the performance metrics, algorithms for determining the fatigue levels of the individuals, algorithms for determining positive performance increases by the individuals, algorithms for determining stress/strain/deflection values for the materials utilized in the wearable devices 115, 125, any other algorithms for performing any other calculations in the system 100, or any combination thereof. In certain embodiments, the database 155 may be configured to store any information generated and/or processed by the system 100, store any of the information disclosed for any of the operations and functions disclosed for the system 100 herewith, store any information traversing the system 100, or any combination thereof. Furthermore, the database 155 may be configured to process queries sent to it by any device in the system 100.

The system 100 may also include a software application, which may be configured to perform and support the operative functions of the system 100. In certain embodiments, the application may be a website, a mobile application, a software application, or a combination thereof, which may be made accessible to users utilizing one or more computing devices, such as first user device 102 and second user device 111. The application of the system 100 may be accessible via an internet connection established with a browser program executing on the first or second user devices 102, 111, a mobile application executing on the first or second user devices 102, 111, or through other suitable means. Additionally, the application may allow users and computing devices to create accounts with the application and sign-in to the created accounts with authenticating username and password log-in combinations. The application may include a custom graphical user interface that the first user 101 or second user 110 may interact with by utilizing a web browser executing on the first user device 102 or second user device 111. In certain embodiments, the software application may execute directly as an installed program on the first and/or second user devices 102, 111. The software application may be configured to render and display performance measurements and metrics obtained from the wearable devices 115, 125, enable access to an individual's user profile, enable viewing of the individual's profile and the information contained therein, calculate any of the calculations described in the present disclosure, provide recommendations to an individual to improve performance, provide recommendations to reduce a risk of injury, provide recommendations to reduce fatigue, generate graphs illustrating real-time performance versus baseline data for an individual, and/or provide any of the functionality described for the system 100, the method 1500, and/or the method 1600.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, receiving signals from sensors of the wearable devices 115, 125 including biometric and/or acceleration data obtained while a user is participating in an activity; converting the signals into digital signals; transmitting the digital signals to a computing device (e.g. first user device 102, second user device 111, etc.) for analysis; analyzing the digital signals to determine a performance metric for the user participating in the activity; comparing the performance metric to baseline data for the user; determining if the comparison indicates that the user is fatigued, needs to improve, and/or is at risk for injury during the activity or otherwise; providing notifications and/or alerts based on the fatigue level, need for improvement and/or risk of injury; providing instructions to avoid injury, improve performance, and/or reduce fatigue; and performing any other suitable operations conducted in the system 100 or otherwise. In one embodiment, multiple servers 160 may be utilized to process the functions of the system 100. The server 160 and other devices in the system 100, may utilize the database 155 for storing data about the devices in the system 100 or any other information that is associated with the system 100. In one embodiment, multiple databases 155 may be utilized to store data in the system 100.

Although FIGS. 1-14 illustrates specific example configurations of the various components of the system 100, the system 100 may include any configuration of the components, which may include using a greater or lesser number of the components. For example, the system 100 is illustratively shown as including a first user device 102, a second user device 111, a wearable device 115, a wearable device 125, a communications network 135, a server 140, a server 150, a server 160, and a database 155. However, the system 100 may include multiple first user devices 102, multiple second user devices 111, multiple wearable devices 115, multiple wearable devices 125, multiple communications networks 135, multiple servers 140, multiple servers 150, multiple servers 160, multiple databases 155, or any number of any of the other components inside or outside the system 100. Similarly, the system 100 may include any number of flexible electronic circuits 116 (ribbon material), microcontrollers 117, 128, accelerometers 118, 127, sensors 119, 129, transmitters 120, power sources 121, 130, matrix material 122, housing trays 1201, or any number of any other components in the system 100. Furthermore, in certain embodiments, substantial portions of the functionality and operations of the system 100 may be performed by other networks and systems that may be connected to system 100.

Figure 15:
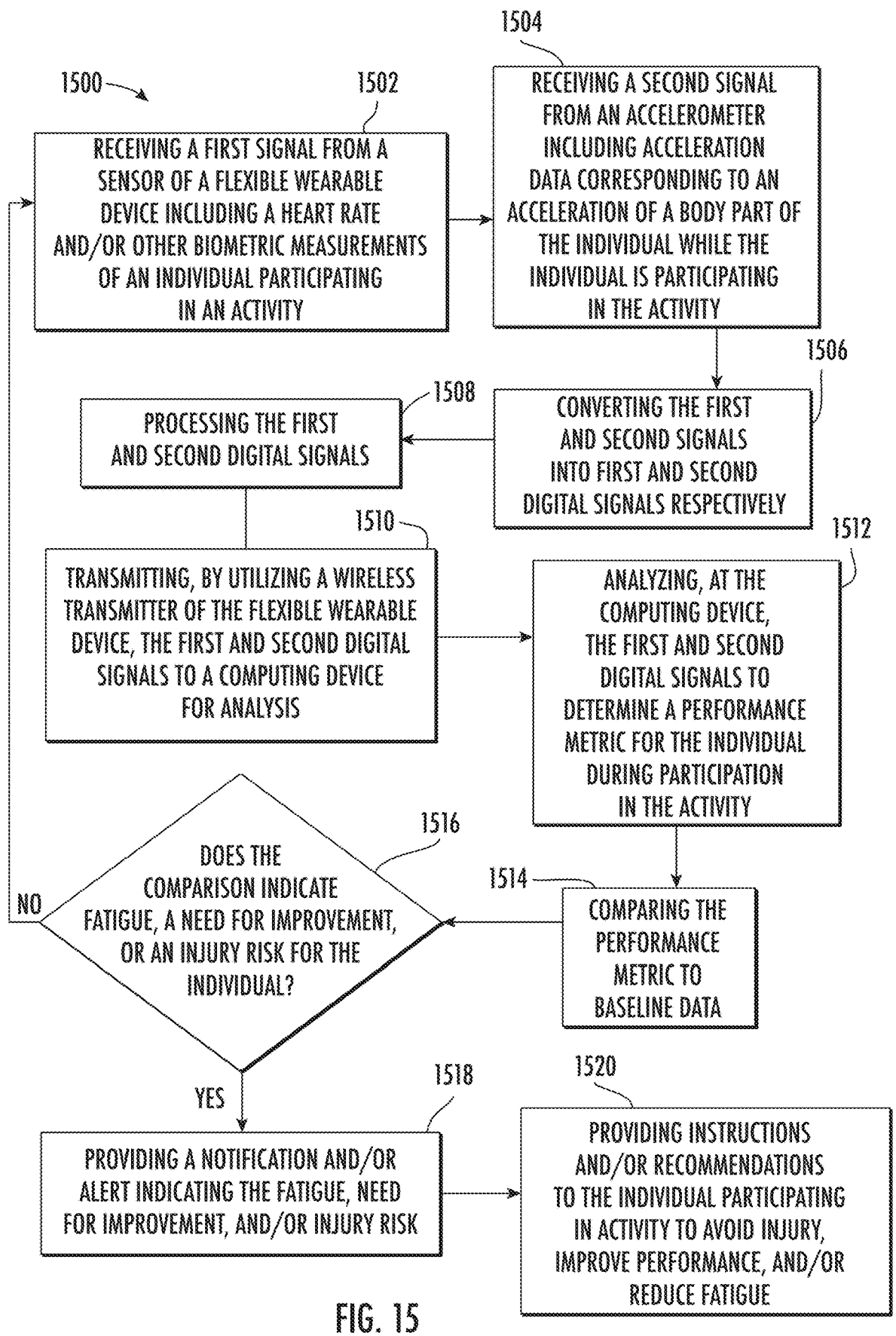
FIG. 15 is a flow diagram illustrating a sample method for utilizing a flexible wearable device according to an embodiment of the present disclosure.

As shown in FIG. 15, an exemplary method 1500 for utilizing a flexible wearable device according to the present disclosure is schematically illustrated. The method 1500 may include, at step 1502, receiving a first signal from a sensor of a flexible wearable device (e.g. wearable devices 115, 125) including one or more biometric measurements of an individual participating in an activity. The sensor may be sensors 119, 129, or any other sensor of the wearable devices 115, 125 and the first signal may be received by the microcontrollers 117, 128 respectively of the wearable devices 115, 125. One or more flexible wearable devices may be worn by the individual on one or more body parts of the individual and may be configured to measure the biometric measurements by utilizing the sensors 119, 129. In certain embodiments, the receiving of the first signal may be performed and/or facilitated by utilizing the wearable device 115, the wearable device 125, the server 140, the server 150, the server 160, the communications network 135, any combination thereof, or by utilizing any other appropriate program, network, system, component, or device. At step 1504, the method 1500 may include receiving a second signal from an accelerometer of the flexible wearable device. The second signal from the accelerometer may include acceleration data (e.g. speed and/or force data) corresponding to one or more accelerations of one or more body parts of the individual participating in the activity. In certain embodiments, the receiving of the second signal may be performed and/or facilitated by utilizing the wearable device 115, the wearable device 125, the server 140, the server 150, the server 160, the communications network 135, any combination thereof, or by utilizing any other appropriate program, network, system, component, or device.

At step 1506, the method 1500 may include converting the first and second signals into first and second digital signals respectively. For example, the first and second signals originally received may be analog signals that are then converted into digital signals at step 1506. In certain embodiments, the converting may be performed and/or facilitated by utilizing the microcontrollers 117, 128, the wearable device 115, the wearable device 125, the server 140, the server 150, the server 160, the communications network 135, any combination thereof, or by utilizing any other appropriate program, network, system, component, or device. At step 1508, the method 1500 may include processing the first and second digital signals. For example, the microcontrollers 117, 128 of each respective wearable device 115, 125 may process the corresponding first and second digital signals received at the microcontrollers 117, 128. In certain embodiments, the processing may be performed and/or facilitated by utilizing the wearable device 115, the wearable device 125, the server 140, the server 150, the server 160, the communications network 135, any combination thereof, or by utilizing any other appropriate program, network, system, component, or device. At step 1510, the method 1500 may include transmitting the first and second digital signals to a computing device for analysis.

For example, the first and second digital signals may be transmitted via the transmitter 120 of the wearable device 115 to the first user device 102, the second user device 111, the servers 140, 150, 160, and/or any other computing device. For first and second digital signals of the wearable device 125, the first and second digital signals may be transmitted using the microcontroller 128, which may include a transmitter. In certain embodiments, the transmitting may be performed and/or facilitated by utilizing the wearable device 115, the wearable device 125, the server 140, the server 150, the server 160, the communications network 135, any combination thereof, or by utilizing any other appropriate program, network, system, component, or device.

At step 1512, the method 1500 may include analyzing the first and second digital signals to determine a performance metric for the individual during participation in the activity. The performance metric may include, but is not limited to, a speed at which a body part of the individual is moved, a force at which the body part of the individual contacts another object, an oxygen level of the individual, a heart rate of the individual, a hydration/dehydration level of the individual, a sweat amount of the individual, a blood volume of blood of the individual, a type of movement made by the individual, a stance made by the individual, an amount of force at which another individual or object contacted the individual, a blood pressure of the individual, a medical condition of the individual, any type of biometric metric of the individual, a fatigue level of the individual, or any combination thereof. In certain embodiments, the analyzing may be performed and/or facilitated by utilizing the first user device 102, the second user device 111, the wearable device 115, the wearable device 125, the server 140, the server 150, the server 160, the communications network 135, any combination thereof, or by utilizing any other appropriate program, network, system, component, or device. At step 1514, the method 1500 may include comparing the performance metric to baseline data associated with the individual. The baseline data may be average performance metrics/data for the individual over a period of time and may comprise known values or quantities associated with the individual's average or normal health conditions, average performance abilities, or a combination thereof. The baseline data may also include biographic data of the individual including, but not limited to, height measurements, weight measurements, health conditions, any demographic information, any other information, or any combination thereof. In certain embodiments, the comparing may be performed and/or facilitated by utilizing the first user device 102, the second user device 111, the wearable device 115, the wearable device 125, the server 140, the server 150, the server 160, the communications network 135, any combination thereof, or by utilizing any other appropriate program, network, system, component, or device.

At step 1516, the method 1500 may include determining if the comparison of the performance metric(s) to the baseline data for the individual indicates that the individual is fatigued, is in need of improvement with respect to performing the activity, is at risk for an injury, or any combination thereof. The individual may be fatigued, in need of improvement, at risk of any injury if the performance metric(s) is a threshold deviation, value, or range from the baseline data. In certain embodiments, the determining may be performed by utilizing the first user device 102, the second user device 111, the wearable device 115, the wearable device 125, the server 140, the server 150, the server 160, the communications network 135, any combination thereof, or by utilizing any other appropriate program, network, system, component, or device. The determining, for example, may indicate that a performance metric corresponding to the speed at which the individual is moving their hands during a fight is slower than the baseline data for the individual. As a result, this may indicate that the individual is fatigued. As another example, a performance metric corresponding to the force at which the individual is contacting an object is much greater than the typical baseline data for the individual. In this case, this may indicate that the individual is performing better during the fight than he typically performs—this may be because the individual is throwing harder punches, kicks, or other body-related movements. As yet another example, if the performance metric is associated with a heart rate of the individual and the heart rate is too high in comparison to the baseline data, this may indicate that the individual is at risk for injury or a debilitating medical condition.

If the comparison of the performance metric to the baseline data indicates that the individual is not fatigued, does not need improvement, and/or is not at risk for injury, the method 1500 may proceed back to step 1502 and continue to receive signals including additional biometric measurements as the individual continues to participate in the activity. If, however, the comparison indicates that the individual is fatigued, needs improvement, and/or is at risk for injury, the method 1500 may proceed to step 1518. At step 1518, the method 1500 may include providing a notification and/or alert that indicates that the individual is fatigued, is in need for improvement, and/or has an injury risk. In certain embodiments, the generating and providing of the notification may be performed and/or facilitated by utilizing the first user device 102, the second user device 111, the wearable device 115, the wearable device 125, the server 140, the server 150, the server 160, the communications network 135, any combination thereof, or by utilizing any other appropriate program, network, system, component, or device. At step 1520, the method 1500 may include providing instructions and/or recommendations to the individual participating in the activity to avoid injury, improve performance, and/or reduce fatigue. The recommendations may be tailored based on the specific performance metrics and/or the deviation from the baseline data. In certain embodiments, the recommendations may be pre-programmed based on the performance metric values, however, in certain embodiments, the recommendations may be tailored to the individual based on the individual's information in the system 100. The recommendations, for example, may indicate a manner in which the individual should change their punching, kicking, and/or movement style during and/or after the activity, a food and/or drink item to be taken by the individual, whether the individual should see a trainer and/or physician for evaluation and training, a type of training and/or exercise regimen to improve their performance, whether the individual is to take a certain type of medicine or supplement, whether the individual should adjust their breathing and how, any type of recommendation, or a combination thereof. In certain embodiments, the generating and providing of the instructions may be performed and/or facilitated by utilizing the first user device 102, the second user device 111, the wearable device 115, the wearable device 125, the server 140, the server 150, the server 160, the communications network 135, any combination thereof, or by utilizing any other appropriate program, network, system, component, or device. Notably, the method

1500 may further incorporate any of the features and functionality described for the system 100 or as otherwise described herein.

Figure 16:
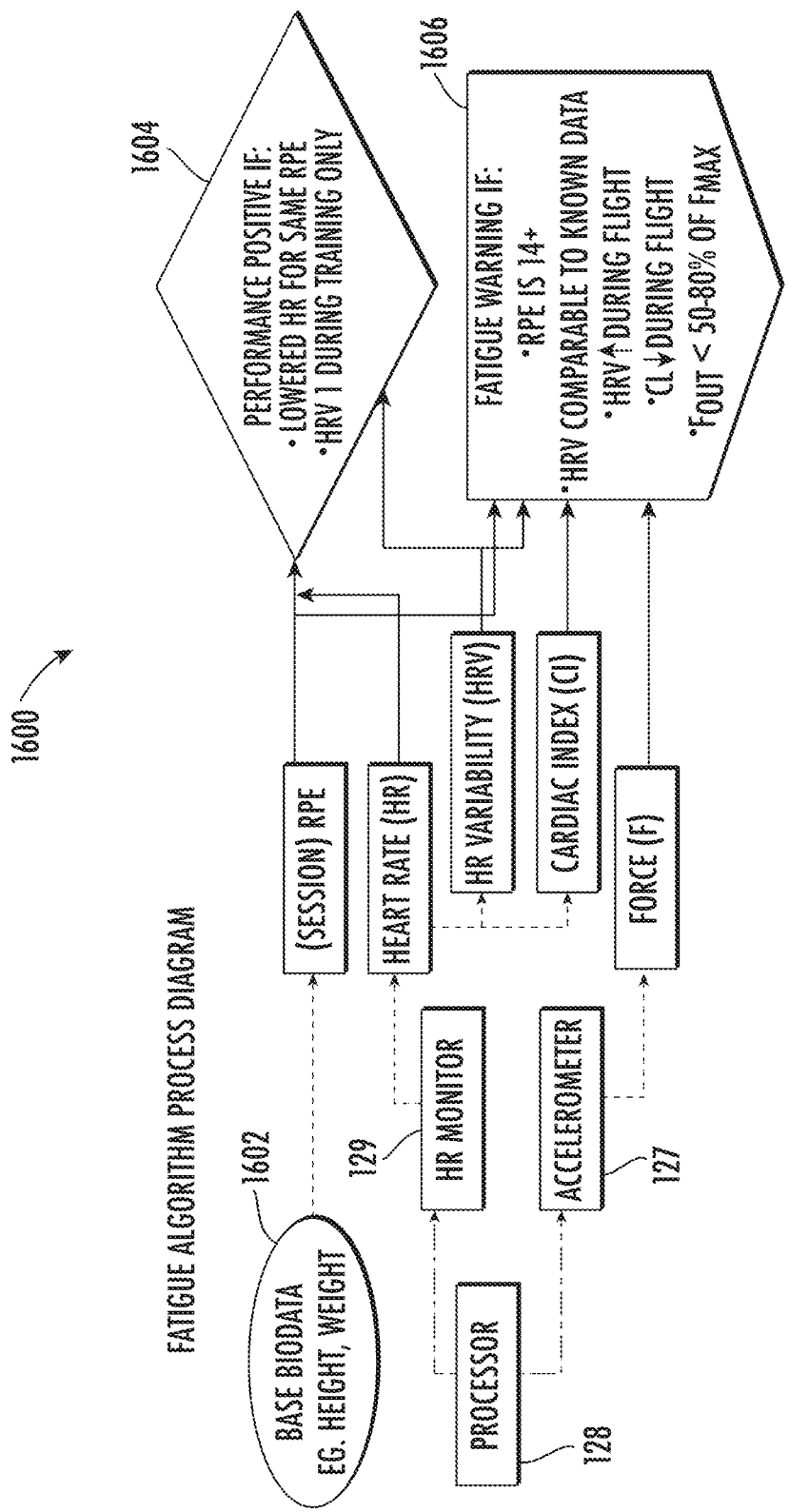
FIG. 16 is a flow diagram illustrating a sample method for utilizing a flexible wearable device to determining fatigue of a user according to an embodiment of the present disclosure.

As shown in FIG. 16, an exemplary method 1600 for utilizing a flexible wearable device (e.g. wearable device 125) to determine fatigue and/or positive performance according to the present disclosure is schematically illustrated. For illustration purposes, wearable device 125 will be utilized with the method 1600, however, wearable device 115 may also be utilized, along with any other desired wearable device. The method 1600 may utilize a several performance/health metrics to estimate the overall fatigue level of an individual. The performance/health metrics may include, but are not limited to, heart rate, heart rate variability, rate of perceived exertion (RPE), cardiac index, heart rate to RPE ratio, and force output. The method 1600 may include, at step 1602, obtaining baseline data for an individual. The baseline data may be average performance metrics/data for the individual over a period of time and may comprise known values or quantities associated with the individual's average or normal health conditions (e.g. normal heart rate, normal blood pressure, normal oxygen levels, normal hydration levels, etc.), average performance abilities (e.g. normal punching speed, normal kicking speed, normal kicking force, normal punching force, normal athletic ability, normal limb movement ranges, etc.), or a combination thereof. The baseline data may also include biographic data of the individual including, but not limited to, height measurements, weight measurements, health conditions, any demographic information, any other information, or any combination thereof. The microcontroller 128 of the wearable device 125 may utilize the sensor 129 (which may be an electrocardiogram circuit or any other sensor configured to measure heart rate or other biometric data) to measure the heart rate of an individual participating in an activity.

As the sensor 129 obtains heart rate measurement values for the individual that is wearing the wearable device 125 while performing an activity, the method 1600 may include calculating a heart rate variability value for the individual. The heart rate variability value may be the variation in the time interval between heartbeats detected by the sensor 129, and may be measured by the variation in the beat-to-beat interval. Additionally, the individual's cardiac index may be determined. The cardiac index may be a measurement indicating how hard the individual's heart is working versus the size of the individual. In certain embodiments, the cardiac index may be determined by dividing the individual's cardiac output by the individuals' body surface area. Furthermore, the individual's RPE may be determined. The RPE may be the training load (or exertion load) measured by a trainer or other individual that is observing the individual during the individual's participation in the activity. In certain embodiments, the RPE may be a subjective way in which to quantify the load placed on the individual during performance of the activity. For example, the RPE may correlate with lack of perceived exertion, moderate exertion, or extreme exertion. In certain embodiments, the RPE may be calculated by multiplying a session intensity value for the individual while the individual is performing the activity by the duration to provide a measure of load in arbitrary units. In certain embodiments, the intensity may be a described as a number, such as 1-10, on the CR-10 RPE scale. Still further, the accelerometer 127 of the wearable device 125 may provide force measurements associated with the individual's movement of limbs or other body parts. The force measurements may be measured in Newtons, PSI, and/or lbf.

Based on the measured and calculated values, the method 1600 may include determining whether the individual's performance metrics and/or measurement values during the activity indicates a positive performance increase as compared to previous performances or whether the individual is at risk for injury or is experiencing fatigue. At step 1604, the method 1600 may determine that the performance is indicative of a positive performance increase if the individual has a lower measured heart rate during the activity for the same RPE as compared with the individual's baseline data or the individual's previous performance for the same activity. At step 1604, the method may also determine that the performance metrics are indicative of a positive performance increase if the heart rate variability value has increased during the individual's training. On the other hand, at step 1606, the method 1600 may include determining that the individual is fatigued is the RPE is above a threshold value, the heart rate variability value is comparable to the baseline data, the heart rate variability value during performance of the activity (e.g. during a fight as opposed to training) has increased, the individuals cardiac index has decreased during performance of the activity, and/or the force output measured by the accelerometer 127 is less than a range of values of the individuals maximum force output. For example, in certain embodiments, the method 1600 may indicate fatigue if the force output in newtons in less than or equal to 50-80% of the individuals maximum force output that has been measured previously or even during the activity.

The systems and methods disclosed herein may include additional functionality and features. For example, data obtained from the wearable devices 115, 125 worn by the first user 101 and other users may be aggregated and provided to leagues and organizations to facilitate the scouting of new prospects by comparing the first user's 101 performance metrics to the other users' performance metrics. The first user's 101 trainer (e.g. second user 110) may record the first user's 101 training session with the second user device 111 via the applications executing on the second user device 111. The recording may include data, such as, but not limited to, force output measurements, speed measurements, types of punches or kicks, types of movements, any other biometric data, or any combination thereof. The recordings may be streamed and/or saved for later playback. In certain embodiments, the wearable devices 115, 125 may also have the capability to assist athletes who participate in forms of martial arts that involve grappling. Pressure sensors in the wearable devices 115, 125 may allow a user to see how much pressure they are applying on chokes with both the arms and the legs. For instance a judoka, Brazilian Jiu-Jitsu practitioner, or wrestler may utilize the device's pressure sensor to see the amount of pressure they are applying while grappling or attempting the various submission moves they attempt. The force data may be compiled with the grappler's biometric data as well while that pairing would also produce fatigue data. This may be important for those in grappling sports as the amount of pressure they apply and how long they can keep that pressure applied without over exerting themselves is key. The grappler may also be able to take advantage of the epidermal electronics ability to determine muscle fatigue and performance. Grapplers may also utilize the system 100 and software applications supporting the system 100 to provide technique feedback as body and limb positioning are pivotal in their form of martial art. Notably, the wearable devices 115, 125 are not only for striking sports, and may be utilized for any type of sport, exercise, activity, or a combination thereof.

Additionally, besides relaying data to tablets, phones, laptops and smart watches, televisions may be set up with software that turns them into touch screens, so while displaying data, members of the gym could use the touch screen to check their corresponding data. The systems and methods may also incorporate voice recognition. For example, voice recognition may be enabled on the wearable devices 115, 125. In an example scenario, a boxer has a glove on and being that the flexible wearable device 115, 125 may be placed under the wrist under the gauze and tape there does remain a small hole on the underside of the glove by which the boxer could lift their hand up and say what activity they are about to undertake because he may be unable to make changes on their phone with gloves on. The systems and methods may utilize artificial intelligence to memorize and analyze movement and, based on movement and stance, the wearable devices 115, 125 and system 100 software will recognize if the boxer is hitting the heavy bag, hitting the speed bag, sparring, etc.

The systems and methods may also include measuring fatigue by breathing on a sensor of flexible wearable devices 115, 125. In certain embodiments, the systems and methods may utilize an algorithm that takes into account where a user's hands and feet are at the same time. For example, the systems and methods may enable one to see that much force you are generating while throwing a punch has a lot to do with the placement of your feet, so being able to see where the feet were exactly while that punch was being thrown could play a lot into technique and coaching. Tracking each limb, regardless of which one is being used, may also be helpful in teaching defenses. Along with other components, GPS or some other form of tracking device that allows trainers and even broadcasters to know the location of the fighter and track their exact placement in the ring relative to their opponent may be incorporated in the wearable devices 115, 125. In certain embodiments, the device and its pressure sensor, along with its ability to read heart rate, will also be pivotal in combat sports like Jiu Jitsu, so the system 100 and wearable devices 115, 125 are not just meant for striking sports.

The wearable devices 115, 125 may be configured to be reusable, and they may also be 3D printable for easier manufacturing and reproduction. There is also the ability to deliver specific supplements to the wearer via a component of the wearable devices 115, 125. In another embodiment, since the wearable devices 115, 125 may be epidermal electronics, this may allow the devices to push different supplements and nutrients through the wearable devices 115, 125 and in through the user's skin. Using the devices sensors to detect the user's biological deficiencies may trigger the software of the system 100 to command various sensors on the device to release the specific vitamin, nutrients or supplements the user's body needs. This may also be accomplished by using a nutritionist to deliver the supplements through use of the software application of the system 100. This could also play into patients that need timed releases of medicine. When not striking, if a user goes out and runs or is doing strength and conditioning, the wearable devices 115, 125 may only utilize the heart rate monitor and may provide the user miles ran, calories burned, oxygen level and hydration level. The stretchable/flexible epidermal electronic devices 115, 125 may be utilized for any sport or activity and the flexible wearable devices 115, 125 may be within kinesiology tape, small band aids, electronic tattoos, smart stickers or smart patches. A heart rate algorithm utilized by the system 100 differs from what is available due to the fact that if the wearable devices 115, 125 can be worn anywhere on the body and in the instance of a combat athlete wearing the device it is best worn on the underside of the wrists and may take calculations from both wrists and in the case of kicking sports both wrists and heels to create a more accurate average. The more a user wears the wearable devices 115, 125 in different areas, the more reliable and accurate the heart rate is and the more the user wears the devices the more data that is aggregated helping the artificial intelligence of the system 100 to identify and create a more in depth profile of the user. The wearable devices 115, 125 can also be worn over the heart for the most accurate reading possible. In certain embodiments, flexible batteries may be utilized with the wearable devices 115, 125, however, energy harvesting batteries may also be utilized. For example, as a taekwondo expert is warming up and shadow boxing/kicking, the wearable devices 115, 125 may be charged and may remain charged as he or she is training.

The systems and methods may include still further functionality and features. In certain embodiments, the wearable devices may be 3D printed and/or printed through a variety of means. The various forms of developing a flexible electronic wearable device 115, 125 allows for a development process of replicating devices through the creation of printing devices or printing stations that takes the place of the manufacturing process. The process may include the use of conductive ink and printing devices similar to home printers or printing devices used to print books or newspapers on a large scale. Printing the wearable flexible devices 115, 125 and having a process that places the sensors on the wearable flexible devices 115, 125 will allow the devices to be disposable (biodegradable) for one time use or one week (or other time period) use. Printing stations can be placed in combat sport gyms allowing for the constant flow of new devices that connect to the platform (e.g. the applications supporting the system 100 functionality). The system 100 could components and/or functionality that provide a vending machine that releases flexible wearable devices as well.

In certain embodiments, the wearable device 115,125 may contain printed Graphene and flexible circuitry. Graphene may be a component utilized for its conductive nature, its ability to repel water and its ability to withstand damage. Graphene-based ink printing devices may be used to print in mass using printers specifically developed to print the devices of the system 100. Sensors may even be graphene-based as well. In another embodiment, the flexible wearable devices 115, 125 may contain a screen via flexible screen technology, LCD, LED, E ink or other screen technologies. In such embodiments, the flexible wearable devices 115, 125 may display on the top of the devices the ongoing real-time data and the user could scroll through via the device's touchscreen to see historical data. A user may utilize the device screen to see their performance and biometric data. In certain embodiments, the wearable device's 115, 125 may have a form factor, which may label them as an electronic, wearable or temporary tattoo. Another term that can be used is sticker or smart sticker to go along with patch, smart patch, and epidermal electronic. Smart stickers can also be made of paper based materials as well. A wearable or temporary tattoo placed on a user could function similarly to a peel and stick children's tattoo or one that water or another liquid assists in the devices adhesion to the user's skin. The process of placing the device on a user could be described as peel and stick. The wearable tattoo or sticker could also change colors depending on the user's biometric state, for example maybe the sticker begins turning red when the wearer's hydration levels are low, or the temporary tattoo or sticker could be customized to incorporate the gym's logo, team logos, or that individual's personal logo and that image could be present from the beginning of training or could show up later to indicate a biometric or performance based goal has been reached, i.e. the devices' colors changing due to the changing of the properties found in the users sweat or other skin related chemical changes. For example, if the user is a kickboxer and the user has reached the point where they are becoming dehydrated, the devices placed on the back of the heel which began the day with a plain white color for example begin to actually show that kickboxers logo, at that point their trainer can either view that information via applications supporting the system 100 or see that image on the stickers are actually fully visible, indicating that it is time for the user to hydrate or wrap up for the day. The wearable tattoo label is befitting of the devices because they adhere to the skin in a way that they do not appear to be a device. The devices may be so flush with the skin they move 1:1 with the skin and appear as if they are an actual tattoo embedded on the user's skin.

In certain embodiments, the system 100 may be utilized to determine fatigue and performance. The adhesive form factor and flexibility of the flexible electronic wearable devices 115, 125 may also be utilized to detect muscle fatigue, muscle tension and overall performance of a muscle group to prevent injury and over training. Given that the wearable devices 115, 125 are flexible electronic systems that adhere directly to the skin, the sensors that are embedded in the wearable devices 115, 125 give the wearables along with the on-board software and the accompanying software application the ability to detect irregularities in muscle movement such as laggard movements, tightness and other such things that are not beneficial to a user and could lead to injury. In certain embodiments, the system and wearable devices 115, 125 may communicatively link with smart devices such as Amazon Echo™ products, Google Home™ products, and/or other various voice-controlled smart-home products. For example a user could walk into their home and ask a smart-home assistant for a breakdown of their training session and the speaker system may give them all of the data the user produced during that days training session. If the user is still wearing the device, the user could ask the user's smart home device what their current heart rate, oxygen level or hydration levels are. These features will also work with the various phone and tablet manufacturers smart assistants like Bixby™ and Siri™, for example. All of the same can be said for smart mirrors and smart home displays as well as smart jewelry, and basically any device or system that displays/relays data.

In certain embodiments, the system 100 and devices of the system 100 may integrate with social media networks. Professional and amateur athletes may have the ability to tie the software application of the system 100 to social media platforms, such as Instagram™ Twitter™, Facebook™, Snapchat™, etc. The athletes will be able to train and engage with their fan base by providing real-time data much like Instagram's™ use of stickers and emoji's, performance and biometric data can be displayed in their Instagram™, Facebook™ or Snapchat™ stories. This feature can also be used by casual users to compete with friends, used by gyms or anyone utilizing the product. In another embodiment, the wearable devices 115, 125, may be utilized in a theme park or water park setting. Functioning similarly to the magic band wearable devices currently used at Disney™ and other theme parks. Utilizing the devices flexibility and adhesive form factor along with a screen display and scanning sensors may allow the devices to adhere to the user's skin while notifying them of ride times, letting them check into the park and onto rides, give them the ability to pay for things within the park. Additionally, it allows the park to locate park goers and collect vital information on where patrons like to reside, what restaurants they frequent most but also allow the park to monitor patrons' health and collect data such as heart rate data to see park goers' emotional reactions to rides and the thrills found within the park.

In certain embodiments, the wearable devices 115, 125 may be configured to work with specialized cameras or other such recording devices that in conjunction would function similarly to the process of motion capture. In certain embodiments, the wearable devices 115, 125 may provide data to gambling prediction platforms by utilizing the system's 100 streams of performance and biometric data. In certain embodiments, the wearable devices 115, 125 can be disposable with a usage of one week or can have one time usage and then it must be disposed of. In such an embodiment, the wearable devices 115, 125 may not require a battery or power source to power the devices, may use the kinetic energy of the user's movement to power the device, or may use potentially solar power before needing to be disposed. In certain embodiments, the wearable devices 115, 125 and the system 100 may provide data on how quickly the fighter's fist extends and how quickly they retract their hand back to their body. The same may go for kicks, how quickly they strike and how quickly they bring their leg back to the ground. Other sets of data the wearable devices 115, 125 and the system 100 can deliver will be the force/speed, amount thrown, amount landed of elbows and knees. Elbow strike data could include, force, speed, and angle. Knee strike data could include the height of the strike, force of strike, speed of strike, angle of strike. In certain embodiments, the system 100 and its components may be 5G compatible and may have compatibility with all possible network changes.

In certain embodiments, the software applications of the system 100 will not only allow coaches to record the fighter they are training, but to hold the device (e.g. first user device 102, such as a phone, tablet, smart watch, and/or smart glasses) up towards the athlete as they are training and see the data displayed on the screen in real-time utilizing an augmented reality feature and also seeing the training session recorded with the augmented-reality-laden data around the athlete they monitored in recorded and stored video. Another capability would be for a training session to be recorded and viewed by coaches or trainers for review in virtual reality. This may allow the coach to watch the athlete they are training from head to toe and every move they make, but with the data floating around the athlete. In certain embodiments, another feature that may be incorporated through the use of the system 100 is filming training, sparring and actual fights in 360 degrees and utilizing sensor data to overlay data on the video all of which will allow trainers to use a virtual reality headsets like the HTC VIVE™, Samsung Gear VR™, Microsoft Holo Lens™, Oculus Rift™ etc to review performance, assess training and game plan with a 360 degree view of the athlete. In certain embodiments, augmented reality devices like Magic Leap™ may also be incorporated into the system 100. In certain embodiments, the system 100 and wearable devices 115, 125 may be configured to recognize users based on profile built of each athlete in the gym from their biometrics to their movements. For example, if the athlete is just placing the device on his or her body, they are automatically connected to the platform of the system 100 and the data automatically begins recording under the appropriate user all through the use of artificial-intelligence and proprietary algorithms.

Another area of placement and another show of how flexible the wearable devices are is a user taking the devices and placing them on the tip of their finger allowing them to get accurate pulse data as well as still gather other biometric and performance based data. In certain embodiments, an optional use of wearable devices 115, 125 is wrapping them around the end of the user's finger to read their fingerprint. In certain embodiments, the wearable devices 115, 125 may be utilized by the military for training purposes and may be utilized to gather biometric data, provide training and actual performance data from on-field operations. In certain embodiments, the components of the system 100 may assist with decision making and battlefield planning based on performance, biometric and health/safety data. In certain embodiments, the wearable devices 115, 125 can be placed anywhere on the user and gather feedback including real-time and historical head impact data by placing the devices on the head and/or neck area to gather rotational data. In certain embodiments, the system 100 may assist the military with a soldier's combat readiness as well as knowing who is fit to be on the field. Historical data can also be utilized by physicians after a combatant has left the military. In certain embodiments, the system 100 may allow for monitoring of military personnel during training and can take that information onto the battle field. The system 100 may provide battle field logistics (GPS), real-time biometrics including, but not limited to, heart rate, body temperature, oxygen level, fatigue level, hydration levels and concussion detection. The system 100 may provide all of the above data, along with combat technique feedback to provide a picture of what is occurring biometrically and physically with military personnel. The system 100 may also be utilized by military boxing teams, martial arts teams, hand-to-hand combat training teams, or any combination thereof. Not only are military personnel able to customize their experience with the wearable devices 115, 125 due to its ability to adhere and stretch with the skin, but they are able to do so with unprecedented levels of comfortability and accuracy. The system 100 facilitates monitoring those out in the field and provides the ability to track performance and how those out in the fields bodies are responding to the conditions and situations they are currently in and how to adapt training for each individual to make sure they are at their peak before entering the field of battle. The system 100 may serve as the testing ground for products that later serve the general public.

In certain embodiments, the wearable devices 115, 125 and the system 100 may be utilized in the medical field. The devices' ability to gather biometric data would make them optimal for emergency room and hospital usage. When a patient checks into a hospital, doctor's office or emergency room they can be handed a sticker (i.e. wearable device 115, 125) that they can place on their bodies that connect to the hospitals monitoring system. Blood pressure monitoring, glucose and oxygen monitoring can be added to these embodiments. Users can have the ability to wear the device and have the data transferred to their physician's office for real-time monitoring or to file away in their medical records. In certain embodiments, the wearable devices 115, 125 may be electronic tattoo—include flexible tattoo like circuits and flexible sensors. Electrical liquid metal alloy and adhesive paper-applicable to the skin using water or other liquids may utilized with the wearable devices 115, 125 as well. In certain embodiments, a longer version of the wearable devices 115, 125 may be utilized, much like kinesiology tape that will allow a user to place a long strip of an adhesive sensor over a muscle group to get feedback on that muscle group or area of the bodies biometric and performance. In certain embodiments, muscle fatigue data gathered by the system 100 will help prevent injuries.

In certain embodiments, the software application of the system 100 and/or the system artificial intelligence may gather data on users every time the wearable device 115, 125 is placed on the users and may continue to aggregate that data offering a personalized experience for every user. The system 100 may incorporate machine learning to constantly learn about each user by finding trends to help optimize the users training, performance and biometric outlook. Data may secured as the wearable device 115, 125 is able to build a complete profile of a user and knows the user and their capabilities so well that over time it has the ability to give coaches suggestions and help come up with game plans, strategies and make pivotal decisions, almost enough to be considered an assistant coach. The system's 100 artificial intelligence may be able to track both the user and, for instance, a competitor the user sparred against tracking every single fine movement from head to toe, even being able to distinguish defense moves like putting hands up block and lifting a leg to check a kick and making constant calculations, assessments and assertions. The system 100 may even evolve to a platform that uses deep learning to provide even more in-depth findings. The system's 100 proprietary algorithms and artificial intelligence can be used on fan versions of the app, for betting platforms, medical research even helping to create automated stories using the data produced to create narratives and fully fleshed data-filled storylines. In certain embodiments, trainers can also utilize the wearable devices 115, 125. For instance if coaches are working on timing with a fighter while they hold the pads the software application of the system 100 will reflect the timing of the fighter's punches or kicks connecting with the pads that the trainer is holding. The software application may show if the fighters are connecting on the pads and throwing the right combinations that the trainer asked them to throw. The system's 100 artificial intelligence learns the combinations and overtime can give feedback on how well that combination landed. The system's 100 artificial intelligence can learn and remember different combinations and will allow coaches to monitor progress or find regression. Coaches wearing the devices can also throw the combinations or specific movements, the software applications detects them throwing it and the software application can compare the athlete the coach is training after they attempt the same combination. Coaches can throw the combinations to input it in the system 100 for the fighter they are training to follow and utilize in training.

In certain embodiments, the system 100 may perform hydration monitoring via the sensors of the wearable devices 115, 125 on the bodies of the users of the system 100. In certain embodiments, glucose and electrolyte measurements may be obtained via the sensors of the wearable devices 115, 125 as well. In certain embodiments, the wearable devices 115, 125 may utilized graphene sensors. In certain embodiments, the system 100 and wearable devices 115, 125 will not only give feedback on force, speed, misses and hits of punches and kicks, but also elbows, and knees. For these metrics, the wearable devices 115, 125 may still be located on the leg or back of the heel for kicks and hand or under wrist for punches, but the devices are able to detect the bending of the arm for elbows and the bending of the leg for knees and the software application of the system 100 may record the appropriate force for each. The system 100 may also track the athlete's movement and the user's foot placement and foot movement. In certain embodiments, the system 100 and wearable devices 115, 125 may be utilized in all types of sports ranging from swimming to ballet, etc. Notably, if there is movement, the system 100 can track the use. Using the wearable devices' 115, 125 form factor, the user-experience is totally customizable and the devices may be placed on any area of the body to gather biometric and performance data. For each different sport, the software application may be tweaked to make it sport-specific. Notably, the functionality and features provided by the system 100 and methods may be utilized for any industry, field-of-use, application, or any combination thereof.

In further embodiments, the wearable devices 115, 125 and the system 100 may be utilized to control a video game. A user may utilize the wearable devices 115, 125 to control a character in a game in virtual reality or on a computer or home console. In essence, the user would become the controller allowing them to run, kick, jump, punch or perform movements with their bodies and extremities with that information being relayed to the video game system all while being interpreted on screen. Electronic skin patches (e.g. wearable devices 115, 125) are the perfect alternative to current hand-held controllers used in a virtual environment, as well as for standard video games because they are non-obtrusive, allow a user to place devices all over their body for complete control of their on screen characters full movement, and/or are capable of adding in biometric readings and tying in the readings into gameplay, which can open up new ways for game developers to involve players or gather feedback on what excites a player. The adhesive the wearable devices 115, 125 may contain haptic feedback that can intensify or lower its feedback depending on the situation as well as the ability to detect movements as exact as which finger a user is pointing, direction, and the user's location in their playing environment The system 100 may add in biometric data such as heart rate for example may add a whole other element to a video game and its storyline and the game could contain elements that would be adapted based on the user's biometric and physiological outlook.

Notably, the system 100 and methods may be utilized with any field-of-use. For example, the system 100 and methods may be utilized with boxing, mixed martial Arts, martial arts, Brazilian Jiu-Jitsu, wrestling, any other sport, or a combination thereof. In certain embodiments, the system 100 may be a software-as-a service (SAAS) platform that may be utilized to sell the wearable devices 115, 125 and more importantly license the data for all patrons within the gym, such as professional and amateur athletes. The data generated by the system 100 may be utilized by trainers, athletes, nutritionists, strength and conditioning coaches and team doctors. The data provided may include, but is not limited to, striking force of punches and kicks, speed of punches and kicks, heart rate, heart rate variability, oxygen level, hydration level, fatigue measurements, technique feedback, and possible concussion detection. The data may be provided in real-time or logged for historical feedback, and may allow for athletes and trainers to game plan for fights, access athlete condition, access athlete performance, prevent injury and overall insure long term health and safety. Aggregated data and the proprietary algorithms of the system 100 may be utilized to create fighter profiles and log each day of training. Additionally, the system 100 may allow for online and retail sales for the data, sporting gear, the wearable devices 115, 125, any component of the system 100, anything else, or a combination thereof.

The system 100 and methods may be utilized in connection with boxing, kickboxing and martial art fitness gyms. The data generated by the system 100 may be utilized by trainers and coaches as well as those attending classes for the purpose of fitness. The data provided may include, but is not limited to, striking force of punches and kicks, speed of punches and kicks, heart rate, heart rate variability, oxygen level, hydration level, fatigue measurements, technique feedback, and possible concussion detection. The system 100 may also allow fitness coaches to access their clients' goals, monitor improvement, and through use of data promote competition, such as via leaderboards. In certain embodiments, the software application utilized of the first and second user devices 102, 111 may also be provided to fans watching an activity performed by a user. The software application may enable fans to visualize fighter or athlete performance via the application itself. In certain embodiments, fans may be provided with real-time data including punches/kicks thrown, punches/kicks landed, the types of punches/kicks thrown, elbow/knees thrown, elbows/knees landed, the force and speed of each type of strike. Fans can even feel the level of anxiety of their favorite fighters by seeing their heart rate in real-time and feel their heart rate through the vibration of their device, which may be triggered via the software application executing on the fan's device. The software application may be used by fans in an arena to get statistics delivered to them in real-time as well, and may also be utilized to fans watching at home via broadcast or through the application itself.

In certain embodiments, the system 100 and methods may be utilized in connection with Olympic combat sports and data may be provided Olympic boxing, taekwondo, judo, wrestling, any other sport, or a combination thereof. The functionality provided by the system 100 may be provided to international clients, may be a tool for Olympic trainers to monitor athletes, and may be a tool for broadcast networks to integrate analytics into Olympic television and/or streaming broadcasts. In certain embodiments, the system 100 and methods may be utilized with various broadcast networks. For example, the data generated by the system 100 may be provided to broadcast networks with data related to a fight or other activity. The system 100 and methods may be utilized to update the antiquated systems currently used by broadcast networks that give the total amount of punches and/or kicks thrown, and what punches and/or kicks landed versus what punches and/or kicks missed. As indicated above, the current statistics gathering standard for all boxing, kickboxing and mixed martial arts broadcasts are CompuBox and CompuStrike. Both use an old method of using human strike counters that watch a fight and tap keys on a keyboard to signify types of punches thrown and what landed. Human error and bias are heavily involved in these older technologies. The system 100 and methods take the bias and human error out of the statistics, while providing greater accuracy. Since many sports are often very subjective due to the way fights are judged, through data the system 100 adds context to every punch and/or kick and/or other body movement. Both broadcast groups and those judging the fight typically make quick visual judgements on which fighter is throwing the harder strikes. The system 100, on the other hand, is able to provide the real-time force and speed of each punch, kick, and/or other body movement.

In further embodiments, the system 100 and methods may be utilized with athletic commissions, such as those that are in charge of fighter safety before and after events. The system 100 may provide data obtained from the wearable devices 115, 125 and/or generated by the system 100 to ensure fighter safety. For example, heart rate, oxygen level, hydration level, and concussion monitoring information may be provided by the system 100. Historical data used by the system 100 allows for long term monitoring of an athletes health and condition, such as concussion-related data that will help commissions determine if a fighter should receive a license to compete. Real-time data provided by the system 100 allows the athletic commission to monitor an athlete's heart rate during a match, their oxygen levels during a match and their hydration levels during a match and most importantly during their strenuous weight cutting process. Real-time functionality provided by the system 100 also includes monitoring the rotational forces placed on each athlete's neck and head area as well. The system 100 and methods may also be utilized for medical research purposes. Currently, there are no real-time biometric readings available nor any devices being used during fights. The system 100 will make real-time biometric data available for medical research groups. For example, the Cleveland Clinic may do a study on concussions in combat sports. They may take baseline information from combat athletes before fights and then perform cognitive tests after fights and compare them against the baseline information. The system 100 may also be utilized to study the impact of the sport on a person's body and mental health. In certain embodiments, the system 100 may provide training data or in-fight data for outcome prediction for sports betting purposes.

In yet further embodiments, the system 100 may be utilized for first responders and/or law enforcement. The system 100 may monitor location, biometric performance, and/or job-specific performance. Performance and biometric monitoring can occur during training our out in the field. In certain embodiments, the system 100 and wearable devices 115, 125 may capture real-time biometric data and the fact that the wearable devices 115, 125 are adhesive allows the quick transfer of data to doctors and medical staff. The system 100 and wearable devices 115, 125 may be utilized in emergency rooms where vital information, such as temperature, heart rate, oxygen level etc. to be collected without staff having to collect that data from each individual. Instead, personnel can give each patient the adhesive wearable devices 115, 1125 to place on their body and that data may be fed right into an application to monitor every individual waiting in the emergency room. In certain embodiments, the system 100 and wearable devices 115, 125 may be used in physical therapy where the patient's biometric data and limb flexion/extension can be observed via the software application of the system 100. In still further embodiments, the system 100 and wearable devices 115, 125 may be utilized in all genres of sports. The electronic adhesive skin patches (e.g. wearable devices 115, 125) that deliver biometric and sport specific performance data can be relevant in every type of sport at all levels. In certain embodiments, the software supporting the functionality of the system 100 may be tweaked for each sport. The functionality provided by the system 100 may help to reduce the risk of injury, provide performance data, and provide data relevant to the long-term health of an athlete. Similarly, the functionality provided by the system 100 may have concussion awareness functionality built into the software application itself, provide fatigue levels, provide hydration monitoring, provide any other information, or a combination thereof.

The systems and methods disclosed herein may include further functionality and features. For example, the operative functions of the system 100 and method may be configured to execute on a special-purpose processor specifically configured to carry out the operations provided by the system 100 and method. Notably, the operative features and functionality provided by the system 100 and method may increase the efficiency of computing devices that are being utilized to facilitate the functionality provided by the system 100 and method 500. For example, through the use of machine learning and artificial intelligence conducted by the system 100 to process the biometric and other data associated with the users, a reduced amount of computer operations need to be performed by the devices in the system 100 using the processors and memories of the system 100 than in other systems. In such a context, less processing power needs to be utilized because the processors and memories do not need perform analyses and operations that have already been learned and/or conducted by the system 100. As a result, there are substantial savings in the usage of computer resources by utilizing the software, functionality, and algorithms provided in the present disclosure.

Notably, in certain embodiments, various functions and features of the system 100 and methods may operate without human intervention and may be conducted entirely by computing devices and/or processes. For example, in certain embodiments, multiple computing devices may interact with devices of the system 100 to provide the functionality supported by the system 100. In certain embodiments, the system 100 and methods may also provide effective computing resource management by utilizing the features and functions described in the present disclosure. For example, in certain embodiments, upon receiving the biometric data and acceleration data (or upon the performance of any other operation as described for the system 100 or the method 500), any selected device in the system 100 may transmit a signal to a computing device receiving or processing such data that only a specific quantity of computer processor resources (e.g. processing power) may be dedicated to processing the data, any other operation conducted by the system 100, or any combination thereof. For example, the signal may indicate an amount of processor cycles of a processor that may be utilized to process the data, and/or specify a selected amount of processing power that may be dedicated to processing the data or any of the operations performed by the system 100. In certain embodiments, a signal indicating the specific amount of computer processor resources or computer memory resources to be utilized for performing an operation of the system 100 may be transmitted from the first and/or second user devices 102, 111 to the various components and devices of the system 100.

In certain embodiments, any device in the system 100 may transmit a signal to a memory device to cause the memory device to only dedicate a selected amount of memory resources to the various operations of the system 100. In certain embodiments, the system 100 and methods may also include transmitting signals to processors and memories to only perform the operative functions of the system 100 and methods at time periods when usage of processing resources and/or memory resources in the system 100 is at a certain value. In certain embodiments, the system 100 and methods may include transmitting signals to the memory devices utilized in the system 100, which indicate which specific portions of the memory should be utilized to store any of the data utilized or generated by the system 100. Notably, the signals transmitted to the processors and memories may be utilized to optimize the usage of computing resources while executing the operations conducted by the system 100. As a result, such features provide substantial operational efficiencies and improvements over existing technologies.

Figure 17:
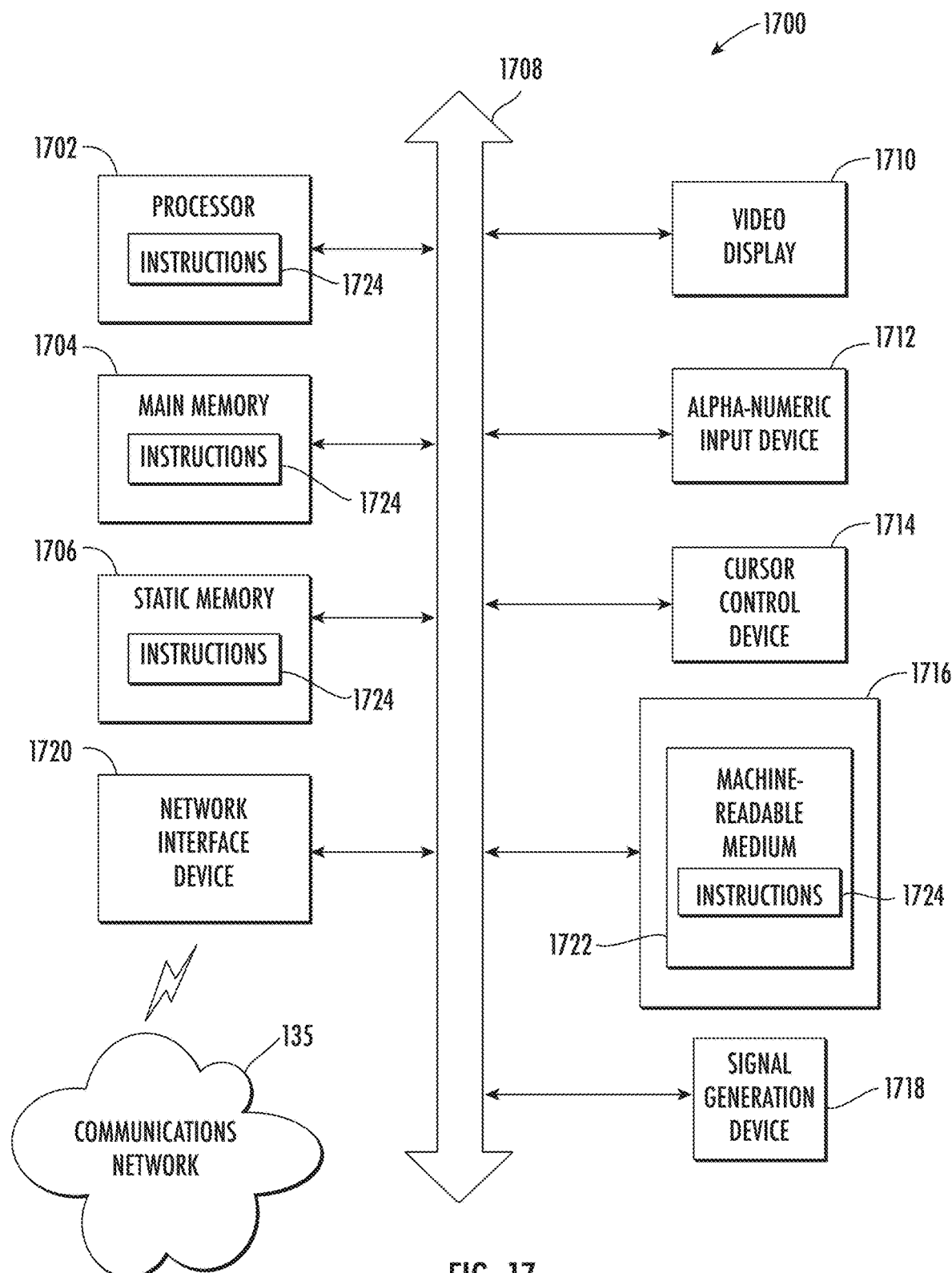
FIG. 17 is a schematic diagram of a machine in the form of a computer system within which a set of instructions, when executed, may cause the machine to perform any one or more of the methodologies or operations of the systems and methods for utilizing a flexible wearable device for measuring performance, fatigue, injury risk, or a combination thereof.

Referring now also to FIG. 17, at least a portion of the methodologies and techniques described with respect to the exemplary embodiments of the system 100 can incorporate a machine, such as, but not limited to, computer system 1700, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the wearable device 115, the wearable device 125, the second user device 111, the server 140, the server 150, the database 155, the server 160, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1700 may include a processor 1702 (e.g., a central processing unit (CPU), a graphics processing unit (GPU, or both), a main memory 1704 and a static memory 1706, which communicate with each other via a bus 1708. The computer system 1700 may further include a video display unit 1710, which may be, but is not limited to, a liquid crystal display (LCD), a flat panel, a solid state display, or a cathode ray tube (CRT). The computer system 1700 may include an input device 1712, such as, but not limited to, a keyboard, a cursor control device 1714, such as, but not limited to, a mouse, a disk drive unit 1716, a signal generation device 1718, such as, but not limited to, a speaker or remote control, and a network interface device 1720.

The disk drive unit 1716 may include a machine-readable medium 1722 on which is stored one or more sets of instructions 1724, such as, but not limited to, software embodying any one or more of the methodologies or functions described herein, including those methods illustrated above. The instructions 1724 may also reside, completely or at least partially, within the main memory 1704, the static memory 1706, or within the processor 1702, or a combination thereof, during execution thereof by the computer system 1700. The main memory 1704 and the processor 1702 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 1722 containing instructions 1724 so that a device connected to the communications network 135, another network, or a combination thereof, can send or receive voice, video or data, and communicate over the communications network 135, another network, or a combination thereof, using the instructions. The instructions 1724 may further be transmitted or received over the communications network 135, another network, or a combination thereof, via the network interface device 1720.

While the machine-readable medium 1722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. A flexible wearable device, comprising:
   a wireless transmitter;
   a sensor configured to measure a heart rate of an individual wearing the wearable device;
   an accelerometer configured to measure an acceleration of a body part of the individual to which the wearable device is attached;
   a flexible power source for providing power to the wearable device;
   a microcontroller including a memory that stores instructions and a processor that executes the instructions to perform operations comprising:
      receiving, from the sensor, a first signal including the heart rate measured by the sensor while the individual is participating in an activity;
      receiving, from the accelerometer, a second signal including acceleration data corresponding to the acceleration of the body part of the individual while the individual is participating in the activity;
      converting the first and second signals into first and second digital signals respectively;
      processing the first and second digital signals;
      transmitting, by utilizing the wireless transmitter, the first and second digital signals to a computing device for analysis, wherein the analysis of the computing device indicates a performance metric of the individual while participating in the activity, wherein the first digital signal, the second digital signal, the performance metric, the analysis, or a combination thereof, are utilized to identify a manner in which a motion of the body part is to be adjusted to reduce or avoid fatigue or an injury risk or improve performance of the activity;
      receiving a notification indicating the manner in which the motion of the body part is to be adjusted;
      processing, at the flexible wearable device, data associated with the motion of the body part after the individual performs the motion of the body part to determine additional motions for the individual to perform over time to further reduce or avoid the fatigue or the injury risk, or improve the performance of the activity; and
   a flexible ribbon, wherein the wireless transmitter, the sensor, the accelerometer, the flexible power source, and the microcontroller are mounted onto the flexible ribbon; and
   a stretchable patch matrix material, wherein the flexible ribbon, the wireless transmitter, the sensor, the accelerometer, the flexible power source, and the microcontroller are housed within a housing tray within the stretchable patch matrix material, wherein the housing tray is covered by the stretchable patch matrix material and air between the housing tray and the stretchable patch matrix material provides insulation for the flexible wearable device.

2. The flexible wearable device of claim 1, further comprising a microneedle for measuring a hydration level of the individual while the individual is participating in the activity.

3. The flexible wearable device of claim 1, wherein the operations further comprise receiving a third signal including an oxygen level measured by the sensor while the individual is participating in the activity.

4. The flexible wearable device of claim 3, wherein the operations further comprise converting the third signal including the oxygen level into a third digital signal, wherein the operations further comprise processing the third digital signal, and wherein the operations further comprise transmitting the third digital signal to the computing device for the analysis.

5. The flexible wearable device of claim 1, further comprising an adhesive incorporated onto a surface of the wearable device which enables the wearable device to be secured to skin of the body part of the individual.

6. The flexible wearable device of claim 1, wherein the operations further comprise receiving a third signal including a number of times the body part has moved during the activity.

7. The flexible wearable device of claim 1, wherein the operations further comprise receiving a third signal including a force at which the body part has moved during the activity.

8. The flexible wearable device of claim 1, wherein the microcontroller comprises a plurality of flexible transistors.

9. The flexible wearable device of claim 1, wherein the operations further comprise transmitting the first and second digital signals to a mobile device, wherein information corresponding to the first and second digital signals is rendered for display on the mobile device.

10. The flexible wearable device of claim 9, wherein the flexible wearable device includes memory foam for insulating the flexible wearable device.

11. The flexible wearable device of claim 1, wherein the flexible wearable device includes viscoelastic plastic for insulating the flexible wearable device.

* * * * *